US007875452B2

(12) United States Patent
Bryant et al.

(10) Patent No.: US 7,875,452 B2
(45) Date of Patent: Jan. 25, 2011

(54) NON-DESENSITIZING MUTANT OF THE TRANSIENT RECEPTOR POTENTIAL TRPM5 ION CHANNEL

(75) Inventors: Robert W. Bryant, Princeton, NJ (US); S. Paul Lee, Yardley, PA (US); Rok Cerne, Lawrenceville, NJ (US); M. N. Tulu Buber, Newtown, PA (US); Ivona Bakaj, Cranbury, NJ (US); Roy Kyle Palmer, Cranbury, NJ (US)

(73) Assignee: Redpoint Bio Corporation, Ewing, NJ (US)

( * ) Notice: Subject to any disclaimer, the term of this patent is extended or adjusted under 35 U.S.C. 154(b) by 0 days.

(21) Appl. No.: 12/285,140

(22) Filed: Sep. 30, 2008

(65) Prior Publication Data

US 2009/0136975 A1 May 28, 2009

Related U.S. Application Data

(60) Provisional application No. 60/976,562, filed on Oct. 1, 2007.

(51) Int. Cl.
*C12N 5/10* (2006.01)
*C12N 15/12* (2006.01)
*C12N 15/63* (2006.01)
*C12N 1/21* (2006.01)

(52) U.S. Cl. .................. 435/325; 435/69.1; 435/252.3; 435/320.1; 536/23.5

(58) Field of Classification Search .................. None
See application file for complete search history.

(56) References Cited

U.S. PATENT DOCUMENTS

| 5,010,175 | A | 4/1991 | Rutter et al. |
| 5,288,514 | A | 2/1994 | Ellman |
| 5,506,107 | A | 4/1996 | Cunningham et al. |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Ashby et al. |
| 5,593,853 | A | 1/1997 | Chen et al. |
| 6,188,965 | B1 | 2/2001 | Mayo et al. |
| 6,269,312 | B1 | 7/2001 | Mayo et al. |
| 6,403,312 | B1 | 6/2002 | Dahiyat et al. |
| 2007/0111264 | A1 | 5/2007 | Bryant et al. |

FOREIGN PATENT DOCUMENTS

| WO | WO 91/19735 A1 | 12/1991 |
| WO | WO 92/00091 A1 | 1/1992 |
| WO | WO 93/20242 A1 | 10/1993 |
| WO | WO 01/25277 A1 | 4/2001 |
| WO | WO 01/32693 A1 | 5/2001 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Baxter, D.F., et al., "A Novel Membrane Potential-Sensitive Fluorescent Dye Improves Cell-Based Assays for Ion Channels," *J. Biomol. Screen.* 7:79-85, Society for Biomolecular Screening (2002).
Campbell, D.A. and Bermak, J.C., "Phosphonate Ester Synthesis Using a Modified Mitsunobu Condensation," *J. Org. Chem.* 59:658-660, American Chemical Society (1994).
Chen, C., et al., "'Analogous' Organic Synthesis of Small-Compound Libraries: Validation of Combinatorial Chemistry in Small-Molecule Synthesis," *J. Am. Chem. Soc.* 116:2661-2662, American Chemical Society (1994).
Cho, C.Y., et al., "An Unnatural Biopolymer," *Science* 261:1303-1305, Association for the Advancement of Science (1993).
Dewitt, S.H., et al., "'Diversomers': An approach to nonpeptide, nonoligomeric chemical diversity," *Proc. Natl. Acad. Sci. U.S.A.* 90:6909-6913, National Academy of Science (1993).
Epps, D.E., et al., "Characterization of the steady-state and dynamic fluorescence properties of the potential-sensitive dye bis-(1,3-dibutylbarbituric acid)trimethine oxonol ($Dibac_4(3)$) in model systems and cells," *Chem. Phys. Lipids* 69:137-150, Elsevier Science (1994).
Evan, G.I., et al., "Isolation of Monoclonal Antibodies Specific for Human c-*myc* Proto-Oncogene Product," *Mol. Cell. Biol.* 5:3610-3616, American Society for Microbiology (1985).
Field, J., et al., "Purification of a RAS-Responsive Adenylyl Cyclase Complex from *Saccharomyces cerevisiae* by Use of an Epitope Addition Method," *Mol. Cell. Biol.* 8:2159-2165, American Society for Microbiology (1988).
Furka, A., et al., "General method for rapid synthesis of multicomponent peptide mixtures," *Int. J. Peptide Protein Res.* 37:487-493, Munksgaard International Publishers (1991).
Gossen, M. and Bujard, H., "Tight control of gene expression in mammalian cells by tetracycline-responsive promoters," *Proc. Natl. Acad. Sci. U.S.A.* 89:5547-5551, National Academy of Science (1992).
Hagihara, M., et al., "Vinylogous Polypeptides: An Alternative Peptide Backbone," *J. Am. Chem. Soc.* 114:6568-6570, American Chemical Society (1992).

(Continued)

*Primary Examiner*—Christine J Saoud
*Assistant Examiner*—Jon M Lockard
(74) *Attorney, Agent, or Firm*—Sterne Kessler Goldstein & Fox P.L.L.C.

(57) ABSTRACT

There exists a need in the art for high throughput screening assays that can identify compounds that specifically modulate the activity of fast-acting ion channels, such as TRPM5. Current methods, especially electrophysiological, suffer from a lack of sensitivity, rapid signal loss, low throughput, and are labor intensive. The claimed methods and compositions provide electrophysiology methods that allow prolonged sample testing and fluorescent assays with an optical readout that gives rapid readout of the results, has a high signal to noise background ratio, are easy to use, can be modified for automation and miniaturization, and provide verification that a compound specifically modulates TRPM5.

8 Claims, 6 Drawing Sheets

OTHER PUBLICATIONS

Hamill, O.P. and Sakmann, B., "Multiple conductance states of single acetylcholine receptor channels in embryonic muscle cells," *Nature* 294:462-464, Nature Publishing Group (1981).

Hirschmann, R., et al., "Nonpeptidal Petidomimetics with a β-D-Glucose Scaffolding. A Partial Somatostatin Agonist Bearing a Close Structural Relationship to a Potent, Selective Substance P Antagonist," *J. Am. Chem. Soc. 114*:9217-9218, American Chemical Society (1992).

Hofmann, T., et al., "TRPM5 Is a Voltage-Modulated and $Ca^{2+}$-Activated Monovalent Selective Cation Channel," *Curr. Biology 13*:1153-1158, Elsevier (2003).

Holm, M.M., et al., "A Binding Site Tyrosine Shapes Desensitization Kinetics and Agonist Potency at GluR2," *J. Biol. Chem. 42*:35469-35476, American Society for Biochemistry and Molecular Biology (Oct. 2005).

Hopp, T.P., et al., "A Short Polypeptide Marker Sequence Useful for Recombinant Protein Identification and Purification," *Biotechnology 6*:1204-1210, Nature Publishing Group (1988).

Horning, M.S. and Mayer, M.L., "Regulation of AMPA Receptor Gating by Ligand Binding Core Dimers," *Neuron 41*:379-388, Cell Press (2004).

Houghten, R.A., et al., "Generation and use of synthetic peptide combinatorial libraries for basic research and drug discovery," *Nature 354*:84-86, Nature Publishing Group (1991).

Kinnamon, S.C., "Taste transduction: a diversity of mechanisms," *Trends Neurosci. 11*:491-496, Elsevier (1988).

Liang, R., et al., "Parallel Synthesis and Screening of a Solid Phase Carbohydrate Library," *Science 274*:1520-1522, Association for the Advancement (1996).

Lutz-Freyermuth, C., et al., "Quantitative determination that one of two potential RNA-binding domains of the A protein component of the U1 small nuclear ribonucleoprotein complex binds with high affinity to stem-loop II of U1 RNA," *Proc. Natl. Acad. Sci. 87*:6393-6397, National Academy of Science (1990).

Margolskee, R.F., "Molecular Mechanisms of Bitter and Sweet Taste Transduction," *J. Biol. Chem. 277*:1-4, The American Society for Biochemistry and Molecular Biology (2002).

Martin, G.A., et al., "GAP Domains Responsible for Ras p21-Dependent Inhibition of Muscarinic Atrial $K^+$ Channel Currents," *Science 255*:192-194, Association for the Advancement of Science (1992).

Misteli, T. and Spector, D.L., "Applications of the green fluorescent protein in cell biology and biotech," *Nat. Biotechnol. 15*:961-964, Nature Publishing Group (1997).

Mojet, J., et al., "Taste Perception with Age: Generic or Specific Losses in Threshold Sensitivity to the Five Basic Tastes," *Chem. Senses 26*:845-860, Oxford University Press (2001).

Paborsky, L.R., et al., "Mammalian cell transient expression of tissue factor for the production of antigen," *Protein Eng. 3*:547-553, Oxford University Press (1990).

Pérez, C.A., et al., "A transient receptor potential channel expressed in taste receptor cells," *Nat. Neurosci. 5*:1169-1176, Nature Publishing Group (2002).

Prawitt, D., et al., "Identification and characterization of *MTR1*, a novel gene with homology to melastatin (*MLSN1*) and the *trp* gene family located in the BWS-WT2 critical region on chromosome 11P15.5 and showing allele-specific expression," *Hum. Mol. Genet. 9*:203-216, Oxford University Press (2000).

Priel, A., et al., "Block of Kainate Receptor Desensitization Uncovers a Key Trafficking Checkpoint," *Neuron 52*:1037-1046, Elsevier (Dec. 2006).

Skinner, R.H., et al., "Use of the Glu-Glu-Phe C-terminal Epitope for Rapid Purification of the Catalytic domain of Normal and Mutant *ras* GTPase-activiating Proteins," *J. Biol. Chem. 266*:14163-14166, American Society for Biochemistry and Molecular Biology (1991).

Stern-Bach, Y., et al., "Agonist Selectivity of Glutamate Receptor Is Specified by Two Domains Structurally Related to Bacterial Amino Acid-Binding Proteins," *Neuron 13*:1345-1357, Cell Press (1994).

Sun, Y., et al., "Mechanism of glutamate receptor desensitization," *Nature 417*:245-253, Macmillan Press (2002).

Vaughan, T.J., et al., "Human Antibodies with Sub-nanomolar Affinities Isolated from a Large Non-immunized Phage Display Library," *Nat. Biotechnol. 14*:309-314, Cell Press (1996).

Zhang, Y., et al., "Coding of Sweet, Bitter, and Umami Tastes: Different Receptor Cells Sharing Similar Signaling Pathways," *Cell 112*:293-301, Cell Press (2003).

Zochowski, M., et al., "Concepts in Imaging and Microscopy: Imaging Membrane Potential With Voltage-Sensitive Dyes," *Biol. Bull. 198*:1-21, Marine Biological Laboratory (2000).

NCBI Entrez, Genbank Report, Accession No. AAP44476 (Entry Date Jun. 2003).

NCBI Entrez, Genbank Report, Accession No. AAP44477 (Entry Date Jun. 2003).

NCBI Entrez, Genbank Report, Accession No. AY280364 (Entry Date Jun. 2003).

NCBI Entrez, Genbank Report, Accession No. AY280365 (Entry Date Jun. 2003).

NCBI Entrez, Genbank Report, Accession No. NM_014555 (Entry Date Nov. 2000).

NCBI Entrez, Genbank Report, Accession No. NM_020277 (Entry Date Jan. 2001).

NCBI Entrez, Genbank Report, Accession No. NP_055370 (Entry Date Nov. 2000).

NCBI Entrez, Genbank Report, Accession No. NP_064673 (Entry Date Jan. 2001).

* cited by examiner

ATGGCGTACTACCATCACCATCACCATCACTCTAGATCAACAAGTTTGTACAAAAAAGCAGGCTCTTTAAAGG
AACCAATTCAGTCGACTGGATCCGGTACCGAATTCGCCACCATGCAGGATGTCCAAGGCCCCCGTCCCGGA
AGCCCCGGGGATGCTGAaGAcCGGCGGGAGCTGGGCTTGCACAGGGGCGAGGTCAACTTTGGAGGGTCTG
GGAAGAAGCGAGGCAAGTTTGTACGGGTGCCGAGCGGAGTGGCCCCGTCTGTGCTCTTTGACCTGCTGCTT
GCTGAGTGGCACCTGCCGGCCCCCAACCTGGTGGTGTCCCTGGTGGGTGAGGAGCAGCCTTTCGCCATGA
AGTCCTGGCTGCGGGATGTGCTGCGCAAGGGGCTGGTGAAGGCGGCTCAGAGCACAGGAGCCTGGATCCT
GACCAGTGCCCTCCGCGTGGGCCTGGCCAGGCACGTCGGGCAGGCCGTGCGCGACCACTCGCTGGCCAG
CACGTCCACCAAGGTCCGTGTGGTTGCTGTCGGCATGGCCTCGCTGGGCCGCGTCCTGCACCGCCGCATT
CTGGAGGAGGCCCAGGAGGATTTTCCTGTCCACTACCCTGAGGATGACGGCGGCAGCCAGGGCCCCCTCT
GTTCACTGGACAGCAACCTCTCCCACTTCATCCTGGTGGAGCCAGGCCCCCGGGGAAGGGCGATGGGCT
GACGGAGCTGCGGCTGAGGCTGGAGAAGCACATCTCGGAGCAGAGGGCGGGCTACGGGGGCACTGGCAG
CATCGAGATCCCTGTCCTCTGCTTGCTGGTCAATGGTGATCCCAACACCTTGGAGAGGATCTCCAGGGCCGT
GGAGCAGGCTGCCCCGTGGCTGATCCTGGTAGGCTCGGGGGGCATCGCCGATGTGCTTGCTGCCCTAGTG
AACCAGCCCCACCTCCTGGTGCCCAAGGTGGCCGAGAAGCAGTTTAAGGAGAAGTTCCCCAGCAAGCATTT
CTCTTGGGAGGACATCGTGCGCTGGACCAAGCTGCTGCAGAACATCACCTCACACCAGCACCTGCTCACCG
TGTATGACTTCGAGCAGGAGGGCTCCGAGGAGCTGGACACGGTCATCCTGAAGGCGCTGGTGAAAGCCTG
CAAGAGCCACAGCCAGGAGCCTCAGGACTATCTGGATGAGCTCAAGCTGGCCGTGGCCTGGGACCGCGTG
GACATCGCCAAGAGTGAGATCTTCAATGGGGACGTGGAGTGGAAGTCCTGTGACCTGGAGGAGGTGATGGT
GGACGCCCTGGTCAGCAACAAACCCGAGTTTGTGCGCCTCTTTGTGGACAACGGCGCAGACGTGGCCGACT
TCCTGACGTATGGGCGGCTGCAGGAGCTCTACCGCTCCGTGTCACGCAAGAGCCTGCTCTTCGACCTGCTG
CAGCGGAAGCAGGAGGAGGCCCGGCTGACGCTGGCCGGCCTGGGCACCCAGCAGGCCCGGGAGCCACCC
GCGGGGCCACCGGCCTTCTCCCTGCACGAGGTCTCCCGCGTACTCAAGGACTTCCTGCAGGACGCCTGCC
GAGGCTTCTACCAGGACGGCCGGCCAGGGGACCGCAGGAGGGCGGAGAAGGGCCCGGCCAAGCGGCCCA
CGGGCCAGAAGTGGCTGCTGGACCTGAACCAGAAGAGCGAGAACCCCTGGCGGGACCTGTTCCTGTGGGC
CGTGCTGCAGAACCGCCACGAGATGGCCACCTACTTCTGGGCCATGGGCCAGGAAGGTGTGGCAGCCGCA
CTGGCTGCCTGCAAAATCCTCAAAGAGATGTCGCACCTGGAGACGGAGGCCGAGGCGGCCCGAGCCACGC
GCGAGGCGAAATACGAGCGGCTGGCCCTTGACCTCTTCTCCGAGTGCTACAGCAACAGTGAGGCCCGCGC
CTTCGCCCTGCTGGTGCGCCGGAACCGCTGCTGGAGCAAGACCACCTGCCTGCACCTGGCCACCGAGGCT
GACGCCAAGGCCTTCTTTGCCCACGACGGCGTTCAGGCCTTCCTGACCAGGATCTGGTGGGGGGACATGG
CCGCAGGCACGCCCATCCTGCGGCTGCTAGGAGCCTTCCTCTGCCCCGCCCTCGTCTATACCAACCTCATC
ACCTTCAGTGAGGAAGCTCCCCTGAGGACAGGCCTGGAGGACCTGCAGGACCTGGACAGCCTGGACACGG
AGAAGAGCCCGCTGTATGGCCTGCAGAGCCGGGTGGAGGAGCTGGTGGAGGCGCCGAGGGCTCAGGGTG
ACCGAGGCCCACGTGCTGTCTTCCTGCTCACACGCTGGCGGAAATTCTGGGGCGCTCCCGTGACTGTGTTC
CTGGGGAACGTGGTCATGTACTTCGCCTTCCTCTTCCTGTTCACCTACGTCCTGCTGGTGGACTTCAGGCCG
CCCCCCcAGGGCCCCTCAGGGCCCGAGGTCACCCTCTACTTCTGGGTCTTTACGCTGGTGCTGGAGGAAAT
CCGGCAGGGCTTCTTCACAGACGAGGACACACACCTGGTGAAGAAGTTCACACTGTATGTGGGGGACAACT
GGAACAAGTGTGACATGGTGGCCATCTTCCTGTTcATCGTGGGTGTCACCTGCAGGATGCTGCCGTCGGCGT
TTGAGGCTGGCCGCACAGTCCTCGCCATGGACTTCATGGTGTTCACGCTGCGGCTGATCCATATCTTTGCCA
TACACAAGCAGCTGGGCCCCAAGATCATCGTGGTAGAGCGCATGATGAAGGACGTCTTCTTCTTCCTCTTCT
TTCTGAGCGTGTGGCTCGTGGCCTACGGTGTCACCACCCAGGCGCTGCTGCACCCCCATGACGGCCGCCT
GGAGTGGATCTTCCGCCGGGTGCTCTACCGGCCCTACCTGCAGATCTTCGGCCAGATCCCACTGGACGAGA
TTGATGAAGCCCGTGTGAACTGCTCCACCCACCCACTGCTGCTGGAGGACTCACCATCCTGCCCCAGCCTC
TATGCCAACTGGCTGGTCATCCTCCTGCTGGTCACCTTCCTGTTGGTCACCAATGTGCTGCTCATGAACCTG
CTCATCGCCATGTTCAGCTACACGTTCCAGGTGGTGCAGGGCAACGCAGACATGTTCTGGAAGTTCCAGCG
CTACAACCTGATTGTGGAGTACCACGAGCGCCCCGCCCTGGCCCCGCCCTTCATCCTGCTCAGCCACCTGA
GCCTGACGCTCCGCCGGGTCTTCAAGAAGGAGGCTGAGCACAAGCGGGAGCACCTGGAGAGAGACCTGCC
AGACCCCCTGGACCAGAAGGTCGTCACCTGGGAGACAGTCCAGAAGGAGAACTTCCTGAGCAAGATGGAGA
AGCGGAGGAGGGACAGCGAGGGGGAGGTGCTGCGGAAAACCGCCCACAGAGTGGACTTCATTGCCAAGTA
CCTCGGGGGGCTGAGAGAGCAAGAAAAGCGCATCAAGTGTCTGGAGTCACAGATCAACTACTGCTCGGTGC
TCGTGTCCTCCGTGGCTGACGTGCTGGCCCAGGGTGGCGGTCCCCGGAGCTCTCAGCACTGTGGCGAGGG
AAGCCAGCTGGTGGCTGCTGACCACAGAGGTGGTTTAGATGGCTGGGAACAACCCGGGGCTGGCCAGCCT
CCCTCGGACACATAG (SEQ ID NO: 1)

FIG. 1

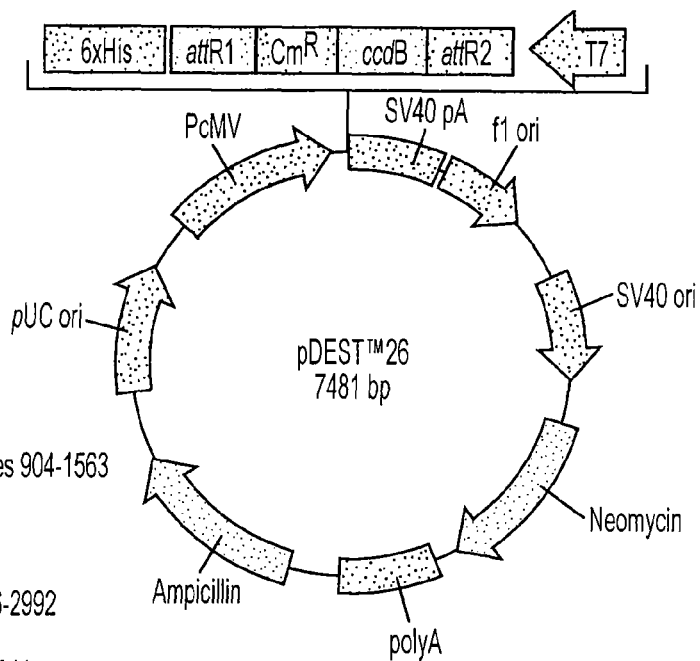

Comments for pDEST™26:
7481 nucleotides

CMV promoter: bases 15-608
6xHis tag: bases 644-661
attR1 site: bases 671-795
Chloramphenicol resistance gene (Cm^R): bases 904-1563
ccdB gene: bases 1905-2210
attR2 site: bases 2251-2375
T7 promoter: bases 2407-2426 (C)
SV40 early polyadenylation signal: bases 2726-2992
f1 intergenic region: bases 3118-3573
SV40 early promoter and origin: bases 3733-4041
Neomycin resistance gene: bases 4100-4894
Synthetic polyadenylation signal: bases 4958-5006
bla promoter: bases 5318-5416
Ampicillin (bla) resistance gene: bases 5417-6277
pUC origin: bases 6422-7095
(C) = complementary strand

FIG. 2A (His)$_6$-hTRPM5 Protein Sequence (SEQ ID NO: 2)

HHHHHHSRSTSLYKKAGSLKEPIQSTGSGTEFAT
MQDVQGPRPGSPGDAEDRRELGLHRGEVNFGGSGKKRGKFVRVPSGVAPSVLFDLLLAEWHLPAP
NLVVSLVGEEQPFAMKSWLRDVLRKGLVKAAQSTGAWILTSALRVGLARHVGQAVRDHSLASTSTK
VRVVAVGMASLGRVLHRRILEEAQEDFPVHYPEDDGGSQGPLCSLDSNLSHFILVEPGPPGKGDGL
TELRLRLEKHISEQRAGYGGTGSIEIPVLCLLVNGDPNTLERISRAVEQAAPWLILVGSGGIADVLAAL
VNQPHLLVPKVAEKQFKEKFPSKHFSWEDIVRWTKLLQNITSHQHLLTVYDFEQEGSEELDTVILKAL
VKACKSHSQEPQDYLDELKLAVAWDRVDIAKSEIFNGDVEWKSCDLEEVMVDALVSNKPEFVRLFV
DNGADVADFLTYGRLQELYRSVSRKSLLFDLLQRKQEEARLTLAGLGTQQAREPPAGPPAFSLHEVS
RVLKDFLQDACRGFYQDGRPGDRRRAEKGPAKRPTGQKWLLDLNQKSENPWRDLFLWAVLQNRH
EMATYFWAMGQEGVAAALAACKILKEMSHLETEAEAARATREAKYERLALDLFSECYSNSEARAFAL
LVRRNRCWSKTTCLHLATEADAKAFFAHDGVQAFLTRIWWGDMAAGTPILRLLGAFLCPALVYTNLIT
FSEEAPLRTGLEDLQDLDSLDTEKSPLYGLQSRVEELVEAPRAQGDRGPRAVFLLTRWRKFWGAPV
TVFLGNVVMYFAFLFLFTYVLLVDFRPPPQGPSGPEVTLYFWVFTLVLEEIRQGFFTDEDTHLVKKFT
LYVGDNWNKCDMVAIFLFIVGVTCRMLPSAFEAGRTVLAMDFMVFTLRLIHIFAIHKQLGPKIIVVERM
MKDVFFFLFFLSVWLVAYGVTTQALLHPHDGRLEWIFRRVLYRPYLQIFGQIPLDEIDEARVNCSTHP
LLLEDSPSCPSLYANWLVILLLVTFLLVTNVLLMNLLIAMFSYTFQVVQGNADMFWKFQRYNLIVEYHE
RPALAPPFILLSHLSLTLRRVFKKEAEHKREHLERDLPDPLDQKVVTWETVQKENFLSKMEKRRRDS
EGEVLRKTAHRVDFIAKYLGGLREQEKRIKCLESQINYCSVLVSSVADVLAQGGGPRSSQHCGEGSQ
LVAADHRGGLDGWEQPGAGQPPSDT

FIG. 2B

COMPARISON OF NATIVE HUMAN TRPM5 (LEFT) AND 6-his TAGGED HUMAN TRPM5 (RIGHT) CONDUCTANCES.
SINGLE CELL PATCH CLAMP (WHOLE-CELL CONFIGURATION);
INTRACELLULAR CALCIUM-ELICITED CHANGES IN CURRENT

SEQUENCE LISTING

```
<160> NUMBER OF SEQ ID NOS: 2

<210> SEQ ID NO 1
<211> LENGTH: 3612
<212> TYPE: DNA
<213> ORGANISM: Artificial Sequence
<220> FEATURE:
```

<223> OTHER INFORMATION: Synthetic coding region for a hexaHis tag and human ion channel TRPM5

<400> SEQUENCE: 1

| | | | | | |
|---|---|---|---|---|---|
| atggcgtact | accatcacca | tcaccatcac | tctagatcaa | caagtttgta | caaaaaagca | 60 |
| ggctctttaa | aggaaccaat | tcagtcgact | ggatccggta | ccgaattcgc | caccatgcag | 120 |
| gatgtccaag | gccccgtcc | cggaagcccc | ggggatgctg | aagaccggcg | ggagctgggc | 180 |
| ttgcacaggg | gcgaggtcaa | ctttggaggg | tctgggaaga | agcgaggcaa | gtttgtacgg | 240 |
| gtgccgagcg | gagtggcccc | gtctgtgctc | tttgacctgc | tgcttgctga | gtggcacctg | 300 |
| ccggccccca | acctggtggt | gtccctggtg | ggtgaggagc | agccttcgc | catgaagtcc | 360 |
| tggctgcggg | atgtgctgcg | caaggggctg | gtgaaggcgg | ctcagagcac | aggagcctgg | 420 |
| atcctgacca | gtgccctccg | cgtgggcctg | gccaggcacg | tcgggcaggc | cgtgcgcgac | 480 |
| cactcgctgg | ccagcacgtc | caccaaggtc | cgtgtggttg | ctgtcggcat | ggcctcgctg | 540 |
| ggccgcgtcc | tgcaccgccg | cattctggag | gaggcccagg | aggattttcc | tgtccactac | 600 |
| cctgaggatg | acggcggcag | ccagggcccc | ctctgttcac | tggacagcaa | cctctcccac | 660 |
| ttcatcctgg | tggagccagg | ccccccgggg | aagggcgatg | ggctgacgga | gctgcggctg | 720 |
| aggctgggaga | agcacatctc | ggagcagagg | gcgggctacg | ggggcactgg | cagcatcgag | 780 |
| atccctgtcc | tctgcttgct | ggtcaatggt | gatcccaaca | ccttggagag | gatctccagg | 840 |
| gccgtggagc | aggctgcccc | gtggctgatc | ctggtaggct | cggggggcat | cgccgatgtg | 900 |
| cttgctgccc | tagtgaacca | gccccacctc | ctggtgccca | aggtggccga | gaagcagttt | 960 |
| aaggagaagt | tccccagcaa | gcatttctct | tgggaggaca | tcgtgcgctg | gaccaagctg | 1020 |
| ctgcagaaca | tcacctcaca | ccagcacctg | ctcaccgtgt | atgacttcga | gcaggagggc | 1080 |
| tccgaggagc | tggacacggt | catcctgaag | gcgctggtga | agcctgcaa | gagccacagc | 1140 |
| caggagcctc | aggactatct | ggatgagctc | aagctggccg | tggcctggga | ccgcgtggac | 1200 |
| atcgccaaga | gtgagatctt | caatggggac | gtggagtgga | agtcctgtga | cctggaggag | 1260 |
| gtgatggtgg | acgccctggt | cagcaacaaa | cccgagtttg | tgcgcctctt | tgtgacaac | 1320 |
| ggcgcagacg | tggccgactt | cctgacgtat | gggcggctgc | aggagctcta | ccgctccgtg | 1380 |
| tcacgcaaga | gcctgctctt | cgacctgctg | cagcggaagc | aggaggaggc | ccggctgacg | 1440 |
| ctggccggcc | tgggcacccca | gcaggcccgg | gagccacccg | cggggccacc | ggccttctcc | 1500 |
| ctgcacgagg | tctcccgcgt | actcaaggac | ttcctgcagg | acgcctgccg | aggcttctac | 1560 |
| caggacggcc | ggccagggga | ccgcaggagg | gcggagaagg | gccggccaa | gcggcccacg | 1620 |
| ggccagaagt | ggctgctgga | cctgaaccag | aagagcgaga | cccctggcg | ggacctgttc | 1680 |
| ctgtgggccg | tgctgcagaa | ccgccacgag | atggccacct | acttctgggc | catgggccag | 1740 |
| gaaggtgtgg | cagccgcact | ggctgcctgc | aaaatcctca | aagagatgtc | gcacctggag | 1800 |
| acggaggccg | aggcggcccg | agccacgcgc | gaggcgaaat | acgagcggct | ggcccttgac | 1860 |
| ctcttctccg | agtgctacag | caacagtgag | gcccgcgcct | tcgccctgct | ggtgcgccgg | 1920 |
| aaccgctgct | ggagcaagac | cacctgcctg | cacctggcca | ccgaggctga | cgccaaggcc | 1980 |
| ttctttgccc | acgacggcgt | tcaggccttc | ctgaccagga | tctggtgggg | gacatggcc | 2040 |
| gcaggcacgc | ccatcctgcg | gctgctagga | gccttcctct | gccccgccct | cgtctatacc | 2100 |
| aacctcatca | ccttcagtga | ggaagctccc | ctgaggacag | gctggagga | cctgcaggac | 2160 |
| ctggacagcc | tggacacgga | gaagagcccg | ctgtatggcc | tgcagagccg | ggtggaggag | 2220 |

-continued

```
ctggtggagg cgccgagggc tcagggtgac cgaggcccac gtgctgtctt cctgctcaca    2280
cgctggcgga aattctgggg cgctcccgtg actgtgttcc tggggaacgt ggtcatgtac    2340
ttcgccttcc tcttcctgtt cacctacgtc ctgctggtgg acttcaggcc gccccccag     2400 ggcccctcag ggcccgaggt caccctctac ttctgggtct tacgctggt gctggaggaa     2460 atccggcagg gcttcttcac agacgaggac acacacctgg tgaagaagtt cacactgtat    2520
gtgggggaca actggaacaa gtgtgacatg gtggccatct cctgttcat cgtgggtgtc     2580 acctgcagga tgctgccgtc ggcgtttgag gctggccgca cagtcctcgc catggacttc    2640
atggtgttca cgctgcggct gatccatatc tttgccatac acaagcagct gggccccaag    2700
atcatcgtgg tagagcgcat gatgaaggac gtcttcttct cctcttctt tctgagcgtg     2760 tggctcgtgg cctacggtgt caccacccag gcgctgctgc accccatga cggccgcctg     2820 gagtggatct ccgccgggt gctctaccgg ccctacctgc agatcttcgg ccagatccca    2880
ctggacgaga ttgatgaagc ccgtgtgaac tgctccaccc acccactgct gctggaggac    2940
tcaccatcct gccccagcct ctatgccaac tggctggtca tcctcctgct ggtcaccttc    3000
ctgttggtca ccaatgtgct gctcatgaac ctgctcatcg ccatgttcag ctacacgttc    3060
caggtggtgc agggcaacgc agacatgttc tggaagttcc agcgctacaa cctgattgtg    3120
gagtaccacg agcgccccgc cctggccccg cccttcatcc tgctcagcca cctgagcctg    3180
acgctccgcc gggtcttcaa gaaggaggct gagcacaagc gggagcacct ggagagagac    3240
ctgccagacc ccctggacca gaaggtcgtc acctgggaga cagtccagaa ggagaacttc    3300
ctgagcaaga tggagaagcg gaggagggac agcgagggg aggtgctgcg gaaaaccgcc    3360
cacagagtgg acttcattgc caagtacctc gggggctga gagagcaaga aaagcgcatc    3420
aagtgtctgg agtcacagat caactactgc tcggtgctcg tgtcctccgt ggctgacgtg    3480
ctggcccagg gtggcggtcc ccggagctct cagcactgtg gcgagggaag ccagctggtg    3540
gctgctgacc acagaggtgg tttagatggc tgggaacaac ccggggctgg ccagcctccc    3600
tcggacacat ag                                                        3612
```

<210> SEQ ID NO 2
<211> LENGTH: 1199
<212> TYPE: PRT
<213> ORGANISM: Artificial Sequence
<220> FEATURE:
<223> OTHER INFORMATION: Synthetic hexaHis tag followed by a 28 amino
      acid linker which is followed by human ion channel TRPM5

<400> SEQUENCE: 2

```
His His His His His His Ser Arg Ser Thr Ser Leu Tyr Lys Lys Ala
1               5                   10                  15

Gly Ser Leu Lys Glu Pro Ile Gln Ser Thr Gly Ser Gly Thr Glu Phe
            20                  25                  30

Ala Thr Met Gln Asp Val Gln Gly Pro Arg Pro Gly Ser Pro Gly Asp
        35                  40                  45

Ala Glu Asp Arg Arg Glu Leu Gly Leu His Arg Gly Glu Val Asn Phe
    50                  55                  60

Gly Gly Ser Gly Lys Lys Arg Gly Lys Phe Val Arg Val Pro Ser Gly
65                  70                  75                  80

Val Ala Pro Ser Val Leu Phe Asp Leu Leu Leu Ala Glu Trp His Leu
                85                  90                  95

Pro Ala Pro Asn Leu Val Val Ser Leu Val Gly Glu Glu Gln Pro Phe
            100                 105                 110
```

-continued

```
Ala Met Lys Ser Trp Leu Arg Asp Val Leu Arg Lys Gly Leu Val Lys
        115                 120                 125
Ala Ala Gln Ser Thr Gly Ala Trp Ile Leu Thr Ser Ala Leu Arg Val
        130                 135                 140
Gly Leu Ala Arg His Val Gly Gln Ala Val Arg Asp His Ser Leu Ala
145                 150                 155                 160
Ser Thr Ser Thr Lys Val Arg Val Ala Val Gly Met Ala Ser Leu
                165                 170                 175
Gly Arg Val Leu His Arg Arg Ile Leu Glu Glu Ala Gln Glu Asp Phe
                180                 185                 190
Pro Val His Tyr Pro Glu Asp Gly Gly Ser Gln Gly Pro Leu Cys
            195                 200                 205
Ser Leu Asp Ser Asn Leu Ser His Phe Ile Leu Val Glu Pro Gly Pro
        210                 215                 220
Pro Gly Lys Gly Asp Gly Leu Thr Glu Leu Arg Leu Arg Leu Glu Lys
225                 230                 235                 240
His Ile Ser Glu Gln Arg Ala Gly Tyr Gly Gly Thr Gly Ser Ile Glu
                245                 250                 255
Ile Pro Val Leu Cys Leu Leu Val Asn Gly Asp Pro Asn Thr Leu Glu
                260                 265                 270
Arg Ile Ser Arg Ala Val Glu Gln Ala Ala Pro Trp Leu Ile Leu Val
            275                 280                 285
Gly Ser Gly Gly Ile Ala Asp Val Leu Ala Ala Leu Val Asn Gln Pro
        290                 295                 300
His Leu Leu Val Pro Lys Val Ala Glu Lys Gln Phe Lys Glu Lys Phe
305                 310                 315                 320
Pro Ser Lys His Phe Ser Trp Glu Asp Ile Val Arg Trp Thr Lys Leu
                325                 330                 335
Leu Gln Asn Ile Thr Ser His Gln His Leu Leu Thr Val Tyr Asp Phe
                340                 345                 350
Glu Gln Glu Gly Ser Glu Glu Leu Asp Thr Val Ile Leu Lys Ala Leu
            355                 360                 365
Val Lys Ala Cys Lys Ser His Ser Gln Glu Pro Gln Asp Tyr Leu Asp
370                 375                 380
Glu Leu Lys Leu Ala Val Ala Trp Asp Arg Val Asp Ile Ala Lys Ser
385                 390                 395                 400
Glu Ile Phe Asn Gly Asp Val Glu Trp Lys Ser Cys Asp Leu Glu Glu
                405                 410                 415
Val Met Val Asp Ala Leu Val Ser Asn Lys Pro Glu Phe Val Arg Leu
                420                 425                 430
Phe Val Asp Asn Gly Ala Asp Val Ala Asp Phe Leu Thr Tyr Gly Arg
            435                 440                 445
Leu Gln Glu Leu Tyr Arg Ser Val Ser Arg Lys Ser Leu Leu Phe Asp
        450                 455                 460
Leu Leu Gln Arg Lys Gln Glu Glu Ala Arg Leu Thr Leu Ala Gly Leu
465                 470                 475                 480
Gly Thr Gln Gln Ala Arg Glu Pro Pro Ala Gly Pro Pro Ala Phe Ser
                485                 490                 495
Leu His Glu Val Ser Arg Val Leu Lys Asp Phe Leu Gln Asp Ala Cys
            500                 505                 510
Arg Gly Phe Tyr Gln Asp Gly Arg Pro Gly Asp Arg Arg Ala Glu
        515                 520                 525
```

-continued

```
Lys Gly Pro Ala Lys Arg Pro Thr Gly Gln Lys Trp Leu Leu Asp Leu
            530                 535                 540
Asn Gln Lys Ser Glu Asn Pro Trp Arg Asp Leu Phe Leu Trp Ala Val
545                 550                 555                 560
Leu Gln Asn Arg His Glu Met Ala Thr Tyr Phe Trp Ala Met Gly Gln
                565                 570                 575
Glu Gly Val Ala Ala Ala Leu Ala Ala Cys Lys Ile Leu Lys Glu Met
            580                 585                 590
Ser His Leu Glu Thr Glu Ala Glu Ala Arg Ala Thr Arg Glu Ala
        595                 600                 605
Lys Tyr Glu Arg Leu Ala Leu Asp Leu Phe Ser Glu Cys Tyr Ser Asn
    610                 615                 620
Ser Glu Ala Arg Ala Phe Ala Leu Leu Val Arg Arg Asn Arg Cys Trp
625                 630                 635                 640
Ser Lys Thr Thr Cys Leu His Leu Ala Thr Glu Ala Asp Ala Lys Ala
                645                 650                 655
Phe Phe Ala His Asp Gly Val Gln Ala Phe Leu Thr Arg Ile Trp Trp
            660                 665                 670
Gly Asp Met Ala Ala Gly Thr Pro Ile Leu Arg Leu Leu Gly Ala Phe
            675                 680                 685
Leu Cys Pro Ala Leu Val Tyr Thr Asn Leu Ile Thr Phe Ser Glu Glu
690                 695                 700
Ala Pro Leu Arg Thr Gly Leu Glu Asp Leu Gln Asp Leu Asp Ser Leu
705                 710                 715                 720
Asp Thr Glu Lys Ser Pro Leu Tyr Gly Leu Gln Ser Arg Val Glu Glu
                725                 730                 735
Leu Val Glu Ala Pro Arg Ala Gln Gly Asp Arg Gly Pro Arg Ala Val
            740                 745                 750
Phe Leu Leu Thr Arg Trp Arg Lys Phe Trp Gly Ala Pro Val Thr Val
            755                 760                 765
Phe Leu Gly Asn Val Val Met Tyr Phe Ala Phe Leu Phe Leu Phe Thr
            770                 775                 780
Tyr Val Leu Leu Val Asp Phe Arg Pro Pro Gln Gly Pro Ser Gly
785                 790                 795                 800
Pro Glu Val Thr Leu Tyr Phe Trp Val Phe Thr Leu Val Leu Glu Glu
                805                 810                 815
Ile Arg Gln Gly Phe Phe Thr Asp Glu Asp Thr His Leu Val Lys Lys
            820                 825                 830
Phe Thr Leu Tyr Val Gly Asp Asn Trp Asn Lys Cys Asp Met Val Ala
        835                 840                 845
Ile Phe Leu Phe Ile Val Gly Val Thr Cys Arg Met Leu Pro Ser Ala
    850                 855                 860
Phe Glu Ala Gly Arg Thr Val Leu Ala Met Asp Phe Met Val Phe Thr
865                 870                 875                 880
Leu Arg Leu Ile His Ile Phe Ala Ile His Lys Gln Leu Gly Pro Lys
                885                 890                 895
Ile Ile Val Val Glu Arg Met Met Lys Asp Val Phe Phe Phe Leu Phe
            900                 905                 910
Phe Leu Ser Val Trp Leu Val Ala Tyr Gly Val Thr Thr Gln Ala Leu
            915                 920                 925
Leu His Pro His Asp Gly Arg Leu Glu Trp Ile Phe Arg Arg Val Leu
        930                 935                 940
Tyr Arg Pro Tyr Leu Gln Ile Phe Gly Gln Ile Pro Leu Asp Glu Ile
```

```
                945               950               955               960
Asp Glu Ala Arg Val Asn Cys Ser Thr His Pro Leu Leu Leu Glu Asp
                    965               970               975
Ser Pro Ser Cys Pro Ser Leu Tyr Ala Asn Trp Leu Val Ile Leu Leu
                980               985               990
Leu Val Thr Phe Leu Leu Val Thr Asn Val Leu Leu Met Asn Leu Leu
            995              1000              1005
Ile Ala Met Phe Ser Tyr Thr Phe Gln Val Val Gln Gly Asn Ala
       1010              1015              1020
Asp Met Phe Trp Lys Phe Gln Arg Tyr Asn Leu Ile Val Glu Tyr
       1025              1030              1035
His Glu Arg Pro Ala Leu Ala Pro Pro Phe Ile Leu Leu Ser His
       1040              1045              1050
Leu Ser Leu Thr Leu Arg Arg Val Phe Lys Lys Glu Ala Glu His
       1055              1060              1065
Lys Arg Glu His Leu Glu Arg Asp Leu Pro Asp Pro Leu Asp Gln
       1070              1075              1080
Lys Val Val Thr Trp Glu Thr Val Gln Lys Glu Asn Phe Leu Ser
       1085              1090              1095
Lys Met Glu Lys Arg Arg Asp Ser Glu Gly Glu Val Leu Arg
       1100              1105              1110
Lys Thr Ala His Arg Val Asp Phe Ile Ala Lys Tyr Leu Gly Gly
       1115              1120              1125
Leu Arg Glu Gln Glu Lys Arg Ile Lys Cys Leu Glu Ser Gln Ile
       1130              1135              1140
Asn Tyr Cys Ser Val Leu Val Ser Ser Val Ala Asp Val Leu Ala
       1145              1150              1155
Gln Gly Gly Gly Pro Arg Ser Ser Gln His Cys Gly Glu Gly Ser
       1160              1165              1170
Gln Leu Val Ala Ala Asp His Arg Gly Gly Leu Asp Gly Trp Glu
       1175              1180              1185
Gln Pro Gly Ala Gly Gln Pro Pro Ser Asp Thr
       1190              1195
```

NON-DESENSITIZING MUTANT OF THE TRANSIENT RECEPTOR POTENTIAL TRPM5 ION CHANNEL

CROSS REFERENCE TO RELATED APPLICATION

This application claims the benefit of U.S. Prov. Appl. No. 60/976,562, filed on Oct. 1, 2008, incorporated herein by reference in its entirety.

BACKGROUND OF THE INVENTION

1. Field of the Invention

The present invention relates to a non-desensitizing mutant of the transient receptor potential TRPM5 ion channel. The present invention also relates to a high throughput screening method useful in the identification of compounds that affect taste sensation by modulating the activity of the non-desensitizing mutant TRPM5 ion channel. The screening method, using for example, electrophysiological measurements, allows for rapidly screening compounds during the non-desensitizing TRPM5 ion channel's prolonged activation period. The non-desensitizing mutant TRPM5 ion channel also allows TRPM5 activation to be monitored with assay techniques that require a longer period of ion channel activation. Therefore, the non-desensitizing mutant TRPM5 ion channel does not limit the types of high throughput screening methods that can be employed by its duration of activation.

2. Background

Taste perception not only plays a critical role in the nutritional status of human beings, but is also essential for the survival of both lower and higher animals (Margolskee, R. F. *J. Biol. Chem.* 277:1-4 (2002); Avenet, P. and Lindemann, B. *J. Membrane Biol.* 112:1-8 (1989)). Taste perception is carried out by taste receptor cells (TRCs). TRCs perceive the multitude of compounds that are associated with a given taste, and convert that perception to a signal deciphered by the brain, resulting in sweet, bitter, sour, salty, or umami (savory) taste.

TRCs are polarized epithelial cells, meaning they have specialized apical and basolateral membranes. Taste buds contain 60-100 TRCs, each having a tiny portion of its membrane exposed on the mucosal surface of the tongue (Kinnamon, S. C. *TINS* 11:491-496 (1988)). Sensory transduction is initiated by sapid molecules, or "tastants," that interact with microvillar processes on the apical membrane of TRCs. The tastants bind specific membrane receptors, leading to a voltage change across the cell membrane; in turn this depolarizes, or changes the electric potential of the cell, causing transmitter release and excitation of primary gustatory nerve fibers.

Ion channels are transmembrane proteins that form pores in a membrane and allow ions to pass from one side to the other (reviewed in B. Hille (Ed), 1992, Ionic Channels of Excitable Membranes 2nd ed., Sinauer, Sunderland, Mass.). Although certain ion channels are open under all physiological membrane conditions (so-called leaky channels), many channels have "gates" that open in response to a specific stimulus. As examples, voltage-gated channels respond to a change in the electric potential across the membrane, mechanically-gated channels respond to mechanical stimulation of the membrane, and ligand-gated channels respond to the binding of specific molecules. Various ligand-gated channels can open in response to extracellular factors, such as neurotransmitters (transmitter-gated channels), or intracellular factors, such as ions (ion-gated channels), or nucleotides (nucleotide-gated channels). Still other ion channels are modulated by interactions with proteins, such as G-proteins (G-protein coupled receptors or GPCRs).

One recently discovered ion channel, TRPM5, has been shown to be essential for taste transduction. Perez et al., *Nature Neuroscience* 5:1169-1176 (2002); Zhang et al., *Cell* 112:293-301 (2003). TRPM5 is a member of the transient receptor potential (TRP) family of ion channels. TRPM5 forms a channel through the membrane of the taste receptor cell, and is believed to be activated by stimulation of a receptor pathway coupled to phospholipase C and by $IP_3$-mediated $Ca^{2+}$ release. The opening of this channel is dependent on a rise in intracellular $Ca^{2+}$ levels. Hofmann et al., *Current Biol.* 13:1153-1158 (2003). The activation of this channel leads to depolarization of the TRC, which in turn leads to transmitter release and excitation of primary gustatory nerve fibers.

Because TRPM5 is a necessary part of the taste-perception machinery, its inhibition prevents an animal from sensing tastes. Although taste perception is a vital function, the inhibition, or masking, of undesirable tastes is beneficial under certain circumstances. For example, many active pharmaceutical ingredients of medicines produce undesirable tastes, such as a bitter taste. Inhibition of the bitter taste produced by the medicine may lead to improved acceptance by the patient. In other circumstances, enhancement of taste may be desirable as in the case of developing improved artificial sweeteners or in treatment of taste losses in groups such as the elderly. Mojet et al., *Chem. Senses* 26:845-60 (2001).

TRPM5 displays voltage modulation and rapid activation/deactivation ("opening and closing") kinetics upon receptor stimulation (Hofmann et al. 2003) which allows for the passage of monovalent cations, such as sodium and potassium. Due to these kinetics, TRPM5 enters a refractory state quickly after activation. In the refractory state, the ion channel does not respond to activating signals, such as voltage modulation. Therefore, in the refractory state, the TRPM5 ion channel is considered to be desensitized. Through proteolytic studies of other non-TRPM5 voltage-gated $Na^+$ and $K^+$ channels, it was concluded that desensitization results from an intrinsic conformational change within the ion channel. This conformational change is considered to be under the control of a channel subunit or region that is separate from the ion channel region which controls activation. (reviewed in E. R. Kandel, 2000, Principles of Neural Science, McGraw-Hill, New York)

The region controlling inactivation and therefore desensitization of ion channel protein regions have been identified through a number of studies employing techniques such as limited chemical fixation and mutagenesis. In the case of the ligand-gated alpha-amino-3-hydroxy-5-methyl-4-isoxazolepropionic acid (AMPA) receptor, it was determined through crystallographic and biochemical studies that certain amino acid substitutions produced non-desensitizing AMPA receptors. The L483Y amino acid substitution attenuates desensitization while strengthening the receptor dimer interface through additional contacts made within the ligand binding core. Similarly, cyclothiazide, an allosteric modulator, was shown to attenuate desensitization of the AMPA receptor by binding to a site formed at a dimer interface acting as a cross-linker stabilizing dimer assembly (See e.g., Mayer, M. L. and Horning, M. S. Neuron 42:379-388 (2004); Stern-Bach, Y. et al., Neuron 13:1345-1357 (1994); Sun, Y. et al., Nature 417:245-253 (2002).) In the case of ligand-gated glutamate receptor GluR2, a single amino acid change in the ion channel polypeptide sequence rendered the ion channel non-desensitizing. A highly-conserved tyrosine residue in GluR2 was observed to be necessary for rapid desensitization. When this tyrosine residue was replaced with a tryptophan amino acid, desensitization was attenuated. (See, e.g., Holm, M. M. et al., *J. Biol. Chem.* 280(42):35469-76 (2005).) The kainate receptors also demonstrate non-desensitization when the binding domain of dimers is stabilized through the generation of intramolecular disulfide bonds. (See, e.g., Priel, A. et al., Neuron 52:1037-1046 (2006).)

One method for testing ion channel activity is to measure changes in cell membrane potential using the patch-clamp technique. (Hamill et al., *Nature* 294:462-4 (1981)). In this technique, a cell is attached to an electrode containing a micropipette tip which directly measures the electrical conditions of the cell. This allows detailed biophysical characterization of changes in membrane potential in response to various stimuli. Thus, the patch-clamp technique can be used as a screening tool to identify compounds that modulate activity of ion channels. This technique is usually time consuming and normally only allows for fewer than two or three compounds per day to be screened for activity.

Methods of screening test compounds can also be high throughput (i.e., allow for many compounds to be screened quickly), automated, easy to use, sensitive, and selective. Screening assays should also provide a high signal to background noise ratio. (Baxter et al., *J. Biomol. Screen.* 7:79-85 (2002)). Background noise is the minimal stimulation that a compound produces regardless of its effect on the ion channel. The high ratio makes visualization of positive or negative modulators simpler because the smallest response will be seen over the background measurements. This leads to a clear identification of modulating compounds.

Therefore, there exists a need in the art for a non-desensitizing TRPM5 ion channel that can deactivate slowly such that HTS assays can distinguish compounds that modulate taste by specifically activating TRPM5. A slowly deactivating ion channel is also useful because more compounds can be tested before the channel closes.

The claimed invention provides compositions and methods for HTS assays using a non-desensitizing TRPM5 ion channel.

BRIEF SUMMARY OF THE INVENTION

In the present invention, a non-desensitizing TRPM5 ion channel is used in HTS assays to identify test compounds that modulate taste by specifically activating TRPM5. The non-desensitizing TRPM5 ion channel is useful in that its activation can be recorded in HTS assays over a longer period of time. The non-desensitizing TRPM5 ion channel is also useful in HTS assays because it allows for more test compounds to be evaluated before the channel closes.

One embodiment of the present invention is directed to isolated polynucleotides encoding a non-desensitizing TRPM5 ion channel.

Another embodiment of the present invention is directed to an isolated host cell that contains an isolated polynucleotide encoding a non-desensitizing TRPM5 ion channel.

Another embodiment of the present invention is directed to an isolated non-desensitizing TRPM5 polypeptide.

In additional embodiments, the non-desensitizing TRPM5 polypeptide is epitope-tagged. In other embodiments, the non-desensitizing TRPM5 polypeptide is amino-terminally epitope-tagged. In further embodiments, the non-desensitizing TRPM5 polypeptide is tagged with a polyhistidine epitope tag.

Another embodiment of the present invention is directed to a recombinant host cell that expresses a non-desensitizing TRPM5 polypeptide.

Another embodiment of the present invention is directed to a method of making an isolated non-desensitizing TRPM5 polypeptide.

Another embodiment of the present invention is a high throughput screening assay for screening potential enhancers of the TRPM5 ion channel comprising contacting a cell expressing a non-desensitizing TRPM5 polypeptide with a suboptimal concentration of an agent that increases intracellular calcium concentration; contacting said cell with a potential enhancing compound; using a patch-clamp apparatus, measuring the membrane current of said cell in the presence of said potential enhancing compound; and comparing the measured membrane current to the membrane current of a different cell expressing a non-desensitizing TRPM5 in the presence of an optimal concentration of an agent that increases intracellular calcium concentration.

Another embodiment of the present invention is a high throughput screening assay for screening potential enhancers of the TRPM5 ion channel comprising contacting a cell expressing a non-desensitizing TRPM5 polypeptide with a suboptimal concentration of an agent that increases intracellular calcium concentration, wherein the cell has been preloaded with a membrane potential fluorescent dye; contacting said cell with a potential enhancing compound; using an optical detector, measuring the fluorescent intensity of said cell in the presence of said potential enhancing compound; and comparing the measured fluorescent intensity to the fluorescent intensity of a different cell expressing a non-desensitizing TRPM5 in the presence of an optimal concentration of an agent that increases intracellular calcium concentration.

In additional embodiments, the claimed method is directed to screening cells that are located in a multi-well vessel. The multi-well vessels of the claimed invention may contain up to and a number equaling 96 wells. In another embodiment, the multi-well vessel comprises greater than 96 wells. In another embodiment, the multi-well vessel comprises 384 wells. In yet another embodiment, the multi-well vessel comprises 1536 wells.

In some embodiments of the claimed invention, agents that increase calcium concentration are selected from the group consisting of: thrombin, adenosine triphosphate (ATP), carbachol, and agonists of endogenous G protein coupled receptors (GPCRs). In one embodiment of the invention, the agent that increases calcium concentration is a calcium ionophore, e.g. A23187, calcimycin or ionomycin.

In some embodiments of the claimed invention, the membrane potential fluorescent dye is a FMP dye.

In additional embodiments of the claimed invention, the optical detector is selected from the group consisting of: Fluorescent Imaging Plate Reader (FLIPR®), FLEXStation™, Voltage/Ion Probe Reader (VIPR™), fluorescent microscope and charge-coupled device (CCD) camera, and Pathway HT™. In one embodiment of the invention, the optical detector is a FLIPR®. In another embodiment, the optical detector is an endpoint microtiter fluorescent reader. Microtiter fluorescent readers may include, but are not limited to, Perkin-Elmer Envision® and Labsystems Fluoroskan II.

Another embodiment of the invention is a high throughput screening assay for determining whether a test compound is a TRPM5 ion channel-specific modulator comprising contacting a cell that expresses a non-desensitizing TRPM5 polypeptide and has been preloaded with a membrane potential fluorescent dye, with a test compound in the presence of potassium chloride; using an optical detector, measuring the fluorescent intensity of said cell in the presence of said potential modulating compound; comparing the measured fluorescent intensity determined above to the fluorescent intensity of a different cell that expresses a non-desensitizing TRPM5 polypeptide and has been preloaded with a membrane potential dye in the presence of potassium chloride and the absence of the test compound; and evaluating whether the test compound may be a TRPM5-specific modulator by determining if the ratio of the fluorescent intensity with KCl and the test compound compared to the intensity with KCl in the absence of the test compound is less than or greater than 1.

Another embodiment of the invention is a high throughput screening assay for determining whether a test compound is a TRPM5 ion channel-specific modulator comprising contacting a cell that expresses a non-desensitizing TRPM5 polypeptide and has been preloaded with an intracellular calcium dye, with a test compound and a suboptimal concentration of a calcium modulating agent that increases intracellular calcium concentration; using an optical detector, measuring the fluorescent intensity of said cell in the presence of said calcium modulating compound; comparing the measured fluorescent intensity determined above to the fluorescent intensity of a different cell that expresses a non-desensitizing TRPM5 polypeptide and has been preloaded with an intracellular calcium dye, in the presence of a suboptimal concentration of a calcium modulating agent and the absence of the test compound; and evaluating whether the test compound may be a TRPM5-specific modulator by determining if the ratio of the fluorescent intensity with a suboptimal concentration of a calcium modulating agent and the test compound, compared to the intensity with a suboptimal concentration of a calcium modulating agent in the absence of the test compound is less than or greater than 1.

In some embodiments, the claimed method further comprises selecting a compound that enhances TRPM5 activity. In further embodiments, the claimed method further comprises selecting a compound that inhibits TRPM5 activity.

Another embodiment of the invention is a high throughput screening assay for determining whether a test compound is a TRPM5 ion channel-specific modulator comprising contacting a cell that expresses a non-desensitizing TRPM5 polypeptide with a suboptimal concentration of an agent that increases intracellular calcium concentration, contacting the cell with a potential enhancing compound, measuring the TRPM5 activity by measuring the membrane potential of the cell in the presence of said potential enhancing compound and comparing that TRPM5 activity to the TRPM5 activity of a different cell expressing a non-desensitizing TRPM5 polypeptide in the presence of an optimal concentration of an agent that increases intracellular calcium concentration.

Another embodiment of the invention is a high throughput screening assay for determining whether a test compound is a TRPM5 ion channel-specific modulator comprising contacting a cell that expresses a non-desensitizing TRPM5 polypeptide with a test compound in the presence of potassium chloride, measuring the TRPM5 activity by measuring the membrane potential of the cell in the presence of said potential modulating compound, comparing the measured TRPM5 activity determined previously to the TRPM5 activity of a different cell that expresses a non-desensitizing TRPM5 polypeptide in the presence of potassium chloride and the absence of the test compound, evaluating whether the test compound may be a TRPM5-specific modulator by determining if the ratio of the membrane potential with potassium chloride and the test compound compared to the membrane potential with potassium chloride in the absence of the test compound is less than or greater than 1. An intensity ratio greater than 1 indicates that the test compound is a TRPM5 enhancer and a ratio less than 1 indicates that the test compound is a TRPM5 inhibitor.

Another embodiment of the invention is a high throughput screening assay for determining whether a test compound is a TRPM5 ion channel-specific enhancer comprising contacting a cell that expresses a non-desensitizing TRPM5 polypeptide with a test compound, measuring TRPM5 activity by measuring the membrane potential of the cell in the presence of said potential enhancing compound, comparing the measured TRPM5 activity determined previously to the TRPM5 activity of a different cell that expresses a non-desensitizing TRPM5 polypeptide in the absence of the test compound, evaluating whether the test compound may be a TRPM5-specific enhancer by determining if the ratio of the activity with the test compound compared to the activity in the absence of the test compound is greater than 1. A ratio greater than 1 indicates that the test compound is a TRPM5 enhancer.

Another embodiment of the invention is a high throughput screening assay for determining whether a test compound is a TRPM5 ion channel-specific inhibitor comprising contacting a cell that expresses a non-desensitizing TRPM5 polypeptide with a test compound in the presence of a known TRPM5 agonist, measuring TRPM5 activity by measuring the membrane potential of the cell in the presence of said potential inhibiting compound, comparing the measured TRPM5 activity determined previously to the TRPM5 activity of a different cell that expresses a non-desensitizing TRPM5 polypeptide in the presence of a known TRPM5 agonist and the absence of the test compound, evaluating whether the test compound may be a TRPM5-specific enhancer by determining if the ratio of the activity with the TRPM5 agonist and the test compound compared to the activity with the TRPM5 agonist in the absence of the test compound is less than 1. A ratio less than 1 indicates that the test compound is a TRPM5 inhibitor.

In some embodiments, the membrane potential of the cell is measured by an ion flux assay or an electrophysiological assay.

In other embodiments, the cell membrane potential of the cell is measured using $Na^+$, $K^+$, $Th^+$, $Li^+$ or $Cs^+$ sensitive membrane potential dyes.

Further embodiments, features, and advantages of the present inventions, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate one or more embodiments of the present invention and, together with the description, further serve to explain the principles of the invention and to enable a person skilled in the pertinent art to make and use the invention.

FIG. 1 shows the cDNA nucleotide sequence encoding amino-terminal polyhistidine epitope tagged TRPM5 (SEQ ID NO: 1).

FIG. 2A shows a map of the pDEST™ 26 vector used to create a non-desensitizing TRPM5 ion channel that has an amino-terminal polyhistidine epitope tag.

FIG. 2B shows the protein sequence of amino-terminal polyhistidine epitope tagged TRPM5 (SEQ ID NO: 2). The polyhistidine epitope tag is linked to the hTRPM5 amino acid sequence by a 28 amino acid linker.

Figure 4:
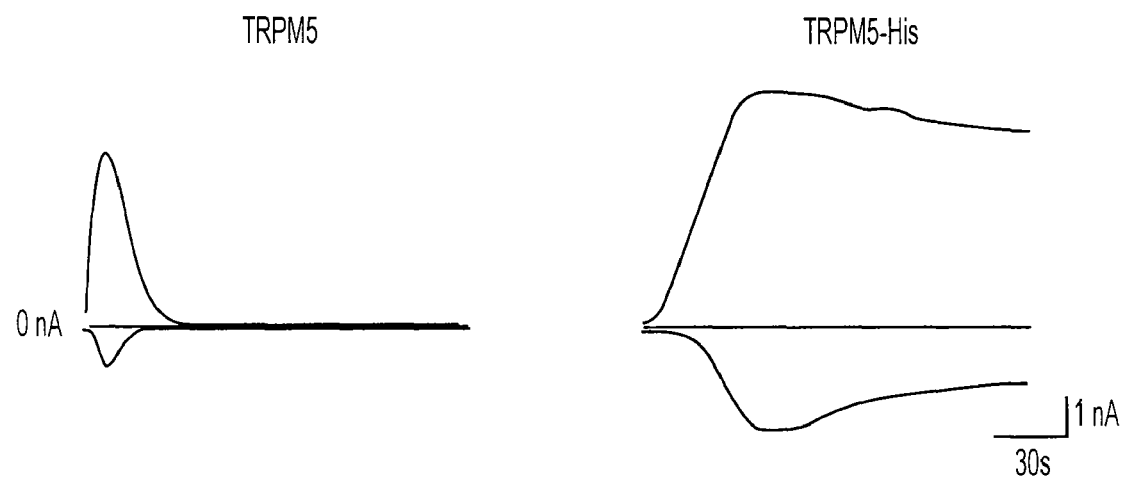

FIG. 4 shows wild-type hTRPM5 and non-desensitizing hTRPM5 ion channel responses in transiently transfected HEK 293 cells through patch-clamp recordings. Panel A shows the patch-clamp (whole-cell configuration) current of HEK 293 cells transfected with wildtype hTRPM5 DNA. The current was activated by Ca$^{2+}$ (1.5 μM) dialysis from the electrode filling solution. The current traces represent the peak current amplitude measured at −80 mV and 80 mV in response to voltage ramps delivered at 1 Hz. Panel B shows the patch-clamp current of HEK 293 cells transfected with non-desensitizing ((His)$_6$-hTRPM5) hTRPM5 DNA.

Figure 5:
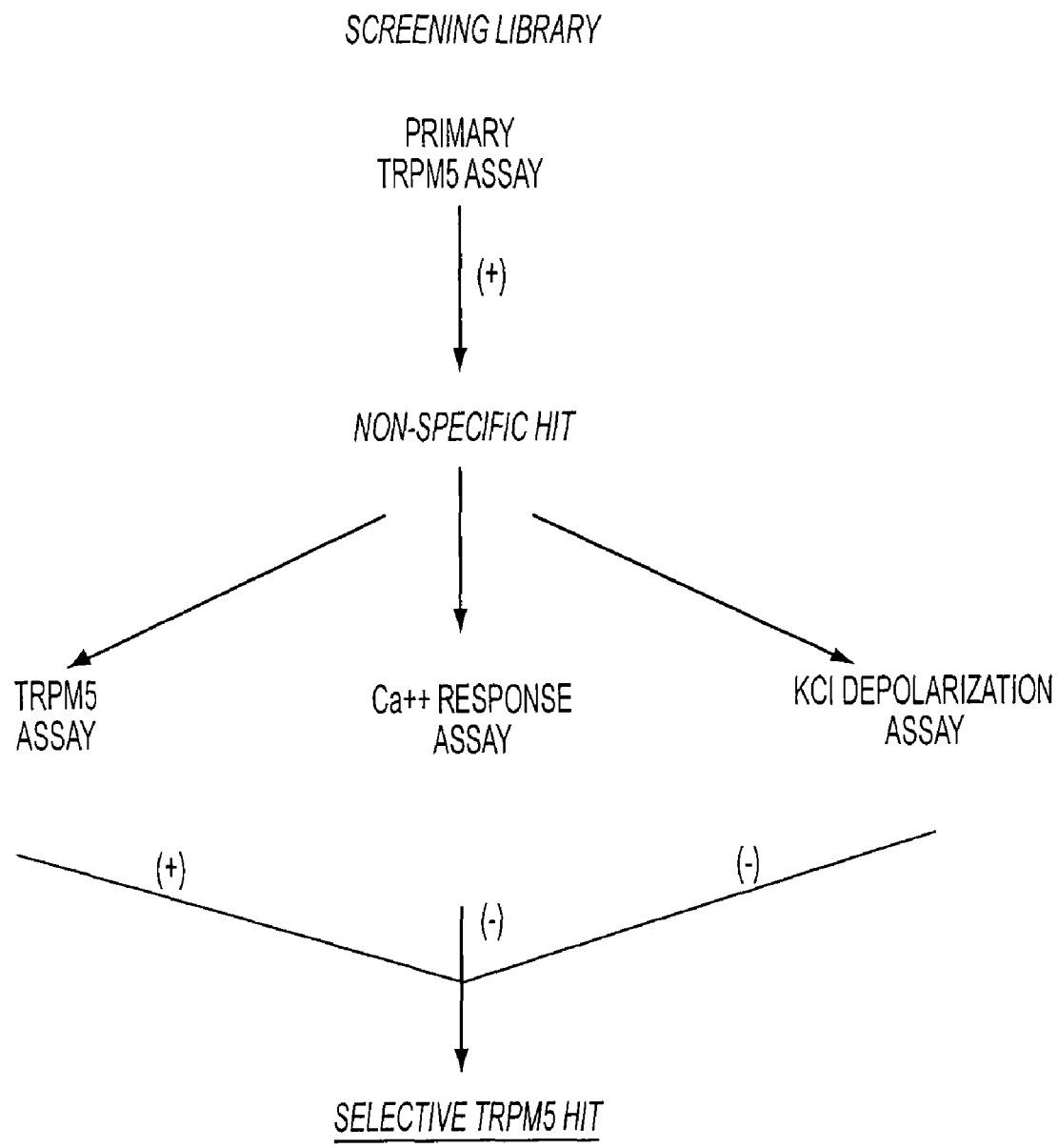

FIG. 5 shows a schematic representation of the TRPM5 specificity filter using Ca$^{2+}$ response and KCl counterscreen assays.

Figure 6:
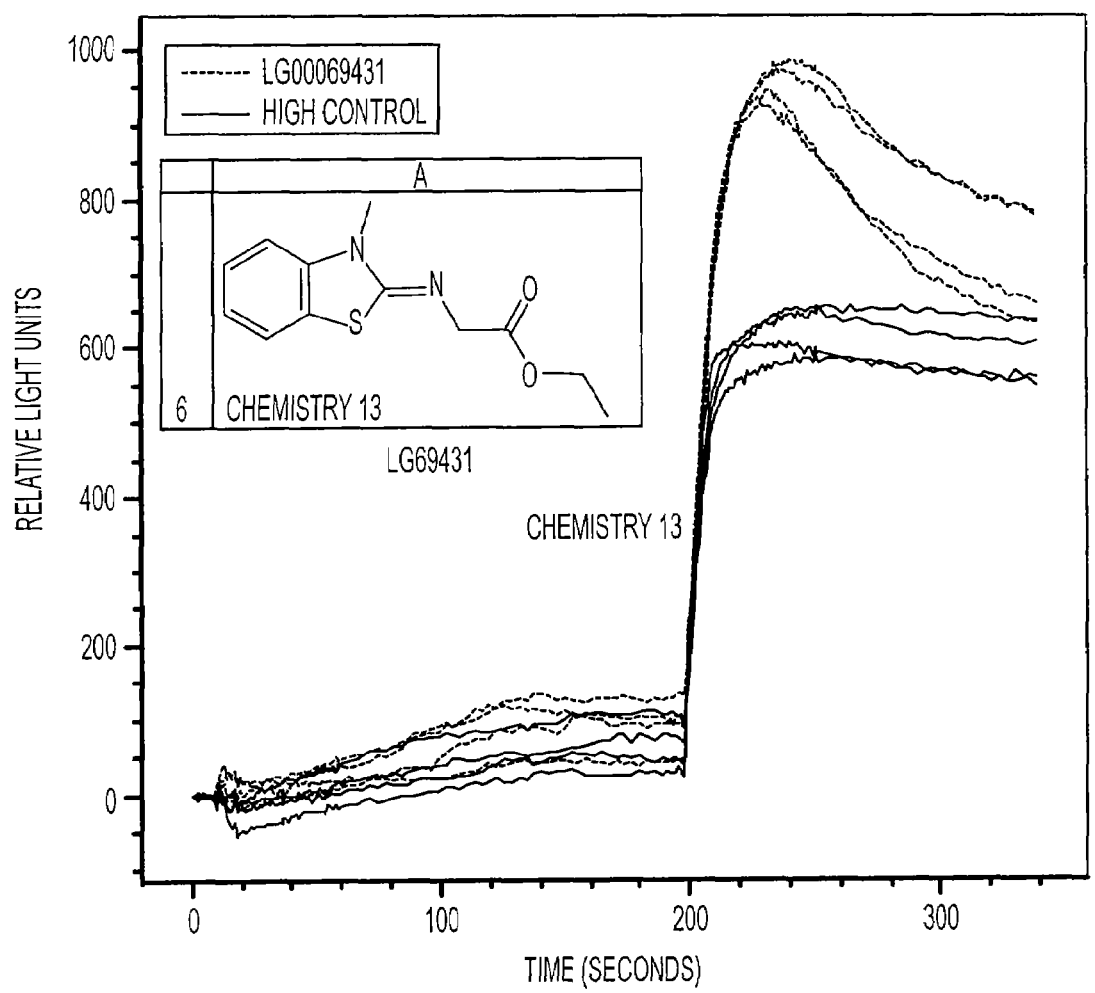

FIG. 6 shows membrane potential responses detected using a FLIPR method in cells transfected with non-desensitizing ((His$_6$-hTRPM5) DNA to the application of High Control (10 μM of ATP) and LG00069431 (12.5 μM). High Control and LG00069431 are applied at 200 seconds. The non-desensitizing TRPM5 ion channel remains open for more than 100 seconds.

DETAILED DESCRIPTION OF THE INVENTION

Overview

The TRPM5 ion channel is a critical downstream signaling protein whose function is required for the sensations of bitter, sweet, and umami taste. When activated by intracellular calcium, the TRPM5 ion channel briefly conducts a sodium current, causing a change in membrane potential, and then rapidly desensitizes, returning the membrane potential to the resting state. Screening assays useful in the identification of TRPM5-specific modulators can be found in U.S. application Ser. No. 11/592,180, which is herein incorporated by reference. The use of non-desensitizing TRPM5 polypeptides in HTS assays offers new opportunities for identifying compounds that specifically interact with TRPM5 and can modulate taste. Since non-desensitizing TRPM5 ion channels close with slower kinetics, they therefore allow for better detection of TRPM5-specific activation and changes in membrane potential attributable to only TRPM5.

By the term "desensitize" is meant to render insensitive or less sensitive to ligands that activate the TRPM5 ion channel. By the term "non-desensitize" or "non-inactivate" is meant to render the TRPM5 ion channel sensitive to ligands that activate the ion channel, such that the TRPM5 ion channel remains activated and open for a longer period of time compared to the wildtype TRPM5 ion channel.

TRPM5 ion channels fall into a class of gated channels that enter a refractory state when exposure to an appropriate ion/ligand is prolonged. Many channels only recover from the refractory state after the cell membrane potential is restored to its original value or the ion/ligand has been removed. (reviewed in E. R. Kandel, 2000, Principles of Neural Science, McGraw-Hill, New York)

In voltage-gated Na$^+$/K$^+$ channels, like TRPM5, desensitization is thought to result from an intrinsic conformational change controlled by a region of the channel that is distinct from that which controls channel activation. (reviewed in E. R. Kandel, 2000, Principles of Neural Science, McGraw-Hill, New York) Therefore, a non-desensitizing TRPM5 ion channel can be made by modifying the region in the ion channel that affects ion channel desensitization and not ion channel activation.

Non-Desensitizing TRPM5 Ion Channel Polynucleotides

In one embodiment, the present invention is directed to an isolated polynucleotide encoding a non-desensitizing TRPM5 ion channel. An "isolated" nucleic acid molecule is one that is separated from other nucleic acid molecules present in the natural source of the nucleic acid. An "isolated" nucleic acid molecule can be, for example, a nucleic acid molecule that is free of at least one of the nucleotide sequences that naturally flank the nucleic acid molecule at its 5' and 3' ends in the genomic DNA of the organism from which the nucleic acid is derived. Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

By the term "nucleic acid sequence" or "nucleotide sequence" or "polynucleotide" is meant the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs. Polynucleotides contemplated in the present invention include, but are not limited to, vectors derived from natural sources or artificially generated.

By the term "vector" or "construct" is meant a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Preferred selectable markers include those which confer resistance to drugs, such as G4181, hygromycin, and methotrexate. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As described herein, the term "TRPM5" refers to a member of the novel family of Ca$^{2+}$ regulated transmembrane channel polypeptides. The TRPM5 gene, encoding the TRPM5 ion channel, is expressed as a 4.5 kb transcript in a variety of fetal and adult tissues (Prawitt et al. *Hum. Mol. Gen.* 9:203-216 (2000)). Human TRPM5 has a putative reading frame containing 24 exons which encode an 1165 amino acid, membrane spanning polypeptide. The National Center for Biotechnology Information (NCBI) database lists several sequences for both the nucleic acid (NP_064673, NP_055370, AAP44477, AAP44476) and amino acid (NM_014555, NM_020277, AY280364, AY280365) sequences for both the human and mouse forms of TRPM5, respectively. The inclusion of the above sequences is for the purpose of illustration of the TRPM5 genetic sequence, however the invention is not limited to one of the disclosed sequences.

By the term "gene" is meant a segment of DNA involved in producing a peptide, polypeptide, or protein, and the mRNA encoding such protein species, including the coding region, and the non-coding regions preceding ("5' UTR") and following ("3' UTR") the coding region. A "gene" may also include intervening non-coding sequences ("introns") between individual coding segments ("exons").

It is recognized in the art that there can be significant heterogeneity in a gene sequence depending on the source of the isolated sequence. The invention contemplates the use of conservatively modified variants of TRPM5. Conservatively modified variants applies to both amino acid and nucleic acid sequences. With respect to nucleic acid sequences, conservatively modified gene variants refer to those polynucleotide sequences which encode identical or essentially identical amino acid sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence.

One skilled in the art will recognize that DNA mutagenesis techniques may be used not only to produce variant DNA molecules encoding non-desensitizing TRPM5 polypeptides, but will also facilitate the production of proteins which differ in certain structural aspects from the TRPM5 ion channel protein. These structurally modified proteins are clearly derivative of the TRPM5 ion channel and maintain most or all of the essential functional characteristics of the TRPM5 ion channel. Newly derived proteins may also be selected in order to obtain variations on the functional characteristic of the TRPM5 protein. Such derivatives include those with variations in amino acid sequence including minor deletions, additions and substitutions.

Amino acid substitutions are typically of single residues; insertions usually will be on the order of about from 1 to 10 amino acid residues; and deletions will range about from 1 to 30 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (See also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The variant DNA molecules encoding non-desensitizing TRPM5 proteins of the invention comprise non-conservative modifications (e.g. substitutions). By "nonconservative" modification herein is meant a modification in which the wildtype encoded amino acid residue and the mutant amino acid residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are nonconservative modifications. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic amino acid residue, e.g. seryl or threonyl, is substituted for (or by) a hydrophobic amino acid residue, e.g. leucyl, isoleucyl, phenylalanyl, valyl or alanyl; (b) a cysteine or proline is substituted for (or by) any other residue; (c) an amino acid residue having an electropositive side chain, e.g. lysyl, arginyl, or histidyl, is substituted for (or by) an electronegative amino acid residue, e.g. glutamyl or aspartyl; or (d) an amino acid residue having a bulky side chain, e.g. phenylalanine, is substituted for (or by) one not having a side chain, e.g. glycine. In one embodiment, the variant DNA molecules encoding a non-desensitizing TRPM5 protein have at least one non-conservative modification.

The variant proteins may be generated, for example, by using a PDA™ system previously described in U.S. Pat. Nos. 6,188,965; 6,296,312; 6,403,312; alanine scanning (see U.S. Pat. No. 5,506,107), gene shuffling (WO 01/25277), site saturation mutagenesis, mean field, sequence homology, polymerase chain reaction (PCR) or other methods known to those of skill in the art that guide the selection of point or deletion mutation sites and types.

Non-desensitizing TRPM5 polypeptides can be generated by substitution of amino acid residues that make contact with TRPM5 ligands and/or line the interior of the ion channel. As in the case of the non-analogous AMPA receptor, crystallographic and biochemical studies can provide information regarding the position and electrostatic nature of residues that make contact with ligands. In one embodiment of the present invention, the non-desensitizing TRPM5 ion channel is generated by substituting the amino acid residues of the ligand-binding region with amino acids that make additional or more favorable contacts with the TRPM5 ligand. The human TRPM5 polypeptide (Genbank Accession Number NP_055370) has six transmembrane helices spanning amino acids 733-755, 770-792, 807-829, 841-863, 871-893 and 955-977 and a putative $Ca^{2+}$ pore spanning amino acids 906-922. (See e.g., Prawitt et al., *Hum. Mol. Gen.* 9:203-216 (2000).) Typically, the last two transmembrane helices flank a loop which determines ion selectivity in ion channel family members that contain 6 transmembrane domains. Amino acid substitution and manipulation in the last two helices and/or loop region can render the TRPM5 polypeptide non-desensitizing. In another embodiment of the present invention, the non-desensitizing TRPM5 ion channel is generated by substituting the amino acid residues of the last two helical transmembrane spanning regions and/or loop region that flank the last two helical transmembrane spanning regions with amino acids that alter the kinetics of ion flow through the ion channel.

As mentioned above, the polynucleotide encoding the TRPM5 ion channel can also be modified with the insertion of amino acids into the TRPM5 polypeptide sequence to render the TRPM5 ion channel non-desensitizing. The insertion can be any length of amino acid, usually 1 to 10 amino acids in length. Therefore, another embodiment of the present invention is directed to an isolated polynucleotide with a first polynucleotide encoding a TRPM5 ion channel or a fragment thereof operably linked to a second polynucleotide encoding additional amino acids, such that the isolated polynucleotide encodes a non-desensitizing TRPM5 ion channel. In a further embodiment, the second polynucleotide encodes 1 to 10 additional amino acids.

By the term "operably linked" is meant a functional relationship between two nucleic acid sequences. For example, a promoter sequence that controls expression (for example, transcription) of a coding sequence is operably linked to that coding sequence. Operably linked nucleic acid sequences can be contiguous, typical of many promoter sequences, or non-contiguous, in the case of, for example, nucleic acid sequences that encode repressor proteins. Within a recombinant expression vector, "operably linked" is intended to mean that the coding sequence of interest is linked to the regulatory sequence(s) in a manner that allows for expression of the coding sequence, e.g., in an in vitro transcription/translation system or in a host cell when the vector is introduced into the host cell.

By the term "promoter" is meant a regulatory sequence of DNA that is involved in the binding of RNA polymerase to initiate transcription of a gene. Promoters are often upstream ("5' to") the transcription initiation site of the gene. A "regulatory sequence" refers to the portion of a gene that can control the expression of the gene. A "regulatory sequence" can include promoters, enhancers and other expression control elements such as polyadenylation signals, ribosome binding site (for bacterial expression), and/or, an operator.

By the term "coding sequence" is meant the portion of a gene that encodes amino acids and the start and stop signals for the translation of the corresponding polypeptide via triplet-base codons.

"Recombinant" refers to a nucleic acid, a protein encoded by a nucleic acid, a cell, or a viral particle, that has been modified using molecular biology techniques to something other than its natural state.

Another embodiment of the present invention is directed to an isolated polynucleotide comprising a first polynucleotide encoding a TRPM5 ion channel or a fragment thereof, operably linked to a second polynucleotide encoding an epitope tag, such that the isolated polynucleotide encodes a non-desensitizing TRPM5 ion channel. By the term "epitope" is meant a portion of a molecule to which an antibody binds. Epitopes can be composed of sugars, lipids or amino acids. In most cases, epitope tags are constructed of amino acids. An epitope tag is generally placed at the amino- or carboxyl-terminus of the TRPM5 ion channel. The presence of such epitope-tagged forms of the TRPM5 ion channel can be detected using an antibody against the tag polypeptide. Also, the epitope tag enables the non-desensitizing TRPM5 ion channel to be readily purified by affinity purification using an anti-tag antibody or another type of affinity matrix that binds to the epitope tag.

For example, polyhistidine epitope tags are often used for affinity purification of polyhistidine-tagged recombinant proteins. Polyhistidine epitope tagged recombinant protein can be purified from cell lysate with affinity media such as nitrilotriacetic acid (NTA)-agarose or Talon resin. These resins utilize metal ions, such as nickel or cobalt, to coordinate and bind polyhistidine epitope tagged recombinant proteins with micromolar affinity. As the primary structure of the polyhistidine epitope tag is the only feature required for binding to the affinity media, the epitope tag is also useful for purifying polyhistidine epitope tagged recombinant proteins under denaturing conditions.

The polyhistidine epitope tag can also be used to detect the presence of the polyhistidine epitope tagged recombinant protein through the use of anti-polyhistidine epitope tag antibodies. These antibodies can be conjugated to fluorescently labeled nitrilotriacetic acid (NTA), such that polyacrylamide gels containing polyhistidine epitope tagged recombinant proteins can be stained and visualized. The antibodies can be used to detect polyhistidine epitope tagged recombinant protein through Western blotting, ELISA and other immunoassays. Finally, these antibodies can also label both prokaryotic and eukaryotic cells such that the subcellular location of the polyhistidine epitope tagged recombinant protein can be determined.

Various tag polypeptides and their respective antibodies are well known in the art. Examples include, but are not limited to, poly-histidine (poly-his) or poly-histidine-glycine (poly-his-gly) tags; the hemagglutinin tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering; 3(6):547-553 (1990)). Other tag polypeptides include the flag-peptide (Hopp et al., BioTechnology, 6:1204-1210 (1988)); the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

In one embodiment, the epitope tag is a polyhistidine tag. In another embodiment, the polyhistidine epitope tag consists of 6, 7, 8, 9, or 10 histidine residues. In another embodiment, the polyhistidine epitope tag consists of 6 histidine residues. In another embodiment, the second polynucleotide encodes an amino-terminal polyhistidine epitope tag.

Non-Desensitizing TRPM5 Ion Channel Polypeptides

To make a non-desensitizing TRPM5 ion channel for use in an HTS method, the non-desensitizing TRPM5 polynucleotide sequence must first be transcribed so that the TRPM5 polypeptide can be translated from the transcribed polynucleotide sequence. Transcription and translation can occur in vitro or in situ. If transcription and translation occur in vivo, a vector can be introduced into a host cell allowing for replication of the vector or for expression of a protein that is encoded by the vector or construct. Therefore, another embodiment of the present invention is directed to a recombinant vector that contains a polynucleotide encoding a non-desensitizing TRPM5 ion channel.

By the term "expression" is meant the translation of the TRPM5 polypeptide from a TRPM5 gene sequence either from a nucleic acid introduced into a cell or from nucleic acid translated in vitro through the use of any of the translation kits known in the art (i.e. Ambion's ActivePro In Vitro Translation Kit). The term "in situ" where used herein includes all these possibilities. Thus, in situ methods may be performed in a suitably responsive cell line which expresses TRPM5 (either as a native channel, or from a nucleic acid introduced into the cell).

It should be noted that expression of non-desensitizing TRPM5 can also be controlled by any of a number of inducible promoters known in the art, such as a tetracycline responsive element, TRE. For example, non-desensitizing TRPM5 can be selectively presented on the cell membrane by controlled expression using the Tet-on™ and Tet-off™ expression systems provided by Clontech (Gossen, M. and Bujard, H. *Proc. Natl. Acad. Sci. USA* 89: 5547-5551 (1992)). In the Tet-on™ system, gene expression is activated by the addition of a tetracycline derivative doxycycline (Dox), whereas in the Tet-off™ system, gene expression is turned on by the withdrawal of tetracyline (Tc) or Dox. Any other inducible mammalian gene expression system may also be used. Examples include systems using heat shock factors, steroid hormones, heavy metal ions, phorbol ester and interferons to conditionally express genes in mammalian cells.

The level of non-desensitizing TRPM5 expression in a cell may be increased by introducing a non-desensitizing TRPM5 nucleic acid into the cells or by causing or allowing expression from a heterologous nucleic acid encoding non-desensitizing TRPM5.

The level of non-desensitizing TRPM5 expression in a cell may be determined by techniques known in the art, including but not limited to, nucleic acid hybridization, polymerase chain reaction, RNase protection, dot blotting, immunocytochemistry and Western blotting. Alternatively, non-desensitizing TRPM5 expression can be measured using a reporter gene system. Such systems, which include for example red or green fluorescent protein (see, e.g. Mistili and Spector, *Nature Biotechnology* 15:961-964 (1997), allow visualization of the reporter gene using standard techniques known to those of skill in the art, for example, fluorescence microscopy. Furthermore, the ability of non-desensitizing TRPM5 to be activated by known positive modulating compounds, such as thrombin, may be determined following manipulation of the non-desensitizing TRPM5 expressing cells.

Another embodiment of the present invention is directed to an isolated host cell that contains a vector encoding a non-desensitizing TRPM5 ion channel, such that the host cell becomes a recombinant host cell. A "recombinant host cell" is a cell that has had introduced into it a recombinant DNA sequence. Recombinant DNA sequences can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila*- and silkworm-derived cell lines. It is further understood that the term "recombinant host cell" refers not only to the subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein. Furthermore, another embodiment of the present invention is directed to a recombinant host cell that expresses a non-desensitizing TRPM5 ion channel.

The cell lines used in assays of the invention may be used to achieve transient expression of non-desensitizing TRPM5, or may be stably transfected with constructs that express a non-desensitizing TRPM5 peptide. Means to generate stably transformed cell lines are well known in the art and such means may be used here. Examples of cells that can be used in assays of the invention include, but are not limited to Chinese Hamster Ovary (CHO) cells, COS-7, HeLa, HEK 293, PC-12, and BAF.

Cells used in assays of the invention described herein may be cultured in any conventional nutrient media. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991).

Another embodiment of the present invention is directed to isolated non-desensitizing TRPM5 ion channel polypeptides. The isolated polypeptides can have amino acid substitutions, insertions or deletions that render the TRPM5 ion channel non-desensitizing. In an embodiment, the non-desensitizing TRPM5 ion channel polypeptide is encoded by any of the isolated polynucleotides described above. In another embodiment, the polypeptides contain an amino-terminal polyhistidine epitope tag.

By the term "polypeptide" or "polypeptide sequence" or "protein sequence" is meant the arrangement of amino acid residues in a polymer. Polypeptide sequences can be composed of the standard 20 naturally occurring amino acids, in addition to rare amino acids and synthetic amino acid analogs. Shorter polypeptides are generally referred to as peptides.

By the terms "isolated" or "purified" protein or "biologically active portion thereof" is meant substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced.

Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest. Isolated biologically active polypeptide can have several different physical forms. The isolated polypeptide can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary. An isolated or substantially purified polypeptide, can be a polypeptide encoded by an isolated nucleic acid sequence, as well as a polypeptide synthesized by, for example, chemical synthetic methods, and a polypeptide separated from biological materials, and then purified, using conventional protein analytical or preparatory procedures. Therefore, another embodiment of the present invention is directed to a method of making an isolated non-desensitizing TRPM5 ion channel polypeptide by culturing a recombinant host cell that has been transfected or transformed with a vector containing a polynucleotide sequence encoding a non-desensitizing TRPM5 ion channel, under conditions such that the polypeptide can be expressed and recovered.

Another embodiment of the present invention is directed to identifying compounds that enhance or inhibit TRPM5 activity. The non-desensitizing TRPM5 ion channel allows for numerous test compounds to be evaluated for their ability to enhance or inhibit TRPM5 activity during the non-desensitizing TRPM5 ion channel's prolonged activation period. The following non-limiting assays serve to illustrate how TRPM5 activity can be measured in the present invention. TRPM5 activity can be measured as a function of cell membrane potential, using membrane potential dyes such as $Na^+$, $K^+$, $Th^+$, $Li^+$, or $Cs^+$ sensitive membrane potential or fluorescent dyes. Cell membrane potential can be measured via an ion flux assay, e.g., using a radiolabeled ion flux assay or an ion flux assay that detects ion flux by atomic absorption spectroscopy. Cell membrane potential can also be measured by electrophysiological methods e.g., patch clamping, automated patch clamping or two electrode voltage clamping techniques. Furthermore, ion channel activity can specifically be attributed to TRPM5 through the use of sham controls.

High-Throughput Screening Assays

Other embodiments of the present invention are directed to a high throughput screening assay for compounds that modulate the activity of TRPM5. Since regulators of TRPM5 are likely to affect taste sensation, the invention, therefore, provides a high throughput screening method useful for the identification of tastants that may specifically modulate TRPM5. This method is more selective than other screens for compounds that may impact taste because this method employs both counterscreening, the use of suboptimal dosing, and prolonged signal detection via a non-desensitizing TRPM5 ion channel. The prolonged signal detection afforded by the non-desensitizing TRPM5 ion channel allows for more compounds to be tested before the channel closes. Such methods can be found in co-pending U.S. application Ser. No. 11/592,080, incorporated herein by reference in its entirety.

High throughput refers to processing many compounds in a short time period. For example, using the invention, numerous test compounds may be screened for the ability to modulate TRPM5 activity in one hour. This assay can be performed using a cell that expresses non-desensitizing TRPM5. As used in the specification and claims, the singular form "a", "an" and "the" include plural references unless the context clearly dictates otherwise. For example, the term "an ion channel" includes a plurality of ion channels. The term "a cell" includes a plurality of cells.

Cells for use in the method of the invention express non-desensitizing TRPM5. The cell is exposed to a test compound and the ability of that compound to stimulate opening or to block opening of the channel is measured. The effect of the test compound is determined by measuring the change in the cell membrane potential after the cell is exposed to the compound. A fluorescent dye that responds to changes in cell membrane potential is used for detection. A means of evaluating specificity of the ability of the compound to modulate the channel is performed in parallel with the above described method. These parallel methods include the use of a potassium chloride counter screen and the use of suboptimal doses of compounds known to stimulate the channel. For more detailed information on using counter screens to evaluate compound specificity for TRPM5, please see U.S. Patent Application Publication 20070111264 A1, hereby incorporated by reference in its entirety.

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

The cells used in methods of the present invention may be cell lines transiently or permanently transfected or transformed with the appropriate proteins or nucleic acids encoding them.

Intracellular Calcium Activation

As discussed above, TRPM5 is a calcium-activated ion channel permeable to monovalent cations such as sodium. Therefore, in order to observe channel activity, calcium stores within the cells must first be activated. There are many methods to activate intracellular calcium stores and many calcium activating agents are known in the art and include, but are not limited to thrombin, adenosine triphosphate (ATP), carbachol, and calcium ionophores (e.g. A23187). While nanomolar increases in calcium concentration ranges are required for TRPM5 channel activation, the concentration ranges useful for the claimed invention are known in the art, e.g., between $10^{-10}$ to $10^{-4}$ M for ATP, however, the precise concentration may vary depending on a variety of factors including cell type and time of incubation. The increased calcium concentration can be confirmed using calcium sensitive dyes, e.g., Fluo 3, Fluo 4, or FLIPR calcium 3 dye and single cell imaging techniques in conjunction with Fura2.

As described below, application of suboptimal doses of calcium activating agents can be used as a secondary screen for non-desensitizing TRPM5 modulating specificity. Test cells are incubated with lower doses of the calcium activating agents described above, such that a fluorescent response that is lower than the maximum achievable response is generated. Generally, the dose is referred to as the effect concentration or $EC_{20-30}$, which relates to the effect condition where the fluorescent intensity is 20-30% of the maximal response. As used herein, "EC" refers to effect condition, such that $EC_{20}$ refers to the effect condition where the fluorescent intensity is 20% of the maximal response is generated. Upon the addition of a TRPM5-specific activating compound, this low response will be increased to at, or near, maximal levels of activation.

Fluorescent Dyes

Voltage sensitive dyes that may be used in the assays and methods of the invention have been used to address cellular membrane potentials (Zochowski et al., *Biol. Bull.* 198:1-21 (2000)). Membrane potential dyes or voltage-sensitive dyes refer to molecules or combinations of molecules that enter depolarized cells, bind to intracellular proteins or membranes and exhibit enhanced fluorescence. These dyes can be used to detect changes in the activity of an ion channel such as TRPM5, expressed in a cell. Voltage-sensitive dyes include, but are not limited to, modified bisoxonol dyes, sodium dyes, potassium dyes and thorium dyes. The dyes enter cells and bind to intracellular proteins or membranes, therein exhibiting enhanced fluorescence and red spectral shifts (Epps et al., *Chem. Phys. Lipids* 69:137-150 (1994)). Increased depolarization results in more influx of the anionic dye and thus an increase in fluorescence.

The non-desensitizing TRPM5 cells of the assay are preloaded with the membrane potential dyes for, for example, 30-240 minutes prior to addition of test compounds. Preloading refers to the addition of the fluorescent dye for a period prior to test compound addition during which the dye enters the cell and binds to intracellular lipophilic moieties.

In one embodiment, the membrane potential dyes are FMP dyes available from Molecular Devices (Catalog Nos. R8034, R8123). In other embodiments, suitable dyes could include dual wavelength FRET-based dyes such as DiSBAC2, DiSBAC3, and CC-2-DMPE (Invitrogen Cat. No. K1016). [Chemical Name Pacific Blue™ 1,2-ditetradecanoyl-sn-glycero-3-phosphoethanolamine, triethylammonium salt]. Cells are typically treated with 1 to 10 µM buffered solutions of the dye for 20 to 60 minutes at 37° C.

Dyes that measure intracellular calcium levels are also used to confirm TRPM5specificity. In one embodiment, the intracellular calcium dye is the FLIPR® Calcium 3 dye available from Molecular Devices (Part Number: R8091). In other embodiments, suitable dyes such as Fluo-3, Fluo-4 (Invitrogen (Cat. Numbers F14242 and F14202) can be used to measure increases in intracellular calcium. Cells are typically treated with 1 to 10 µM buffered solutions of the dye for 20 to 60 minutes at 37° C. In some cases it is necessary to remove the dye solutions from the cells and add fresh assay buffer before proceeding with the assay.

Assay Detection

Detecting and recording alterations in the spectral characteristics of the dye in response to changes in membrane potential may be performed by any means known to those skilled in the art. As used herein, a "recording" refers to collecting and/or storing data obtained from processed fluorescent signals, such as are obtained in fluorescent imaging analysis.

In some embodiments, the assays of the present invention are performed on isolated cells using microscopic imaging to detect changes in spectral (i.e., fluorescent) properties. In other embodiments, the assay is performed in a multi-well format and spectral characteristics are determined using a microplate reader.

By "well" it is meant generally a bounded area within a container, which may be either discrete (e.g., to provide for an isolated sample) or in communication with one or more other bounded areas (e.g., to provide for fluid communication between one or more samples in a well). For example, cells grown on a substrate are normally contained within a well that may also contain culture medium for living cells. Substrates can comprise any suitable material, such as plastic, glass, and the like. Plastic is conventionally used for maintenance and/or growth of cells in vitro.

A "multi-well vessel", as noted above, is an example of a substrate comprising more than one well in an array. Multi-well vessels useful in the invention can be of any of a variety of standard formats (e.g., plates having 2, 4, 6, 24, 96, 384, or 1536, etc., wells), but can also be in a non-standard format (e.g., plates having 3, 5, 7, etc., wells).

A suitable configuration for single cell imaging involves the use of a microscope equipped with a computer system. One example of such a configuration, ATTO's Attofluor® RatioVision® real-time digital fluorescence analyzer from Carl Zeiss, is a completely integrated work station for the analysis of fluorescent probes in living cells and prepared specimens (ATTO, Rockville, Md.). The system can observe ions either individually or simultaneously in combinations limited only by the optical properties of the probes in use. The standard imaging system is capable of performing multiple dye experiments such as FMP (for sodium) combined with GFP (for transfection) in the same cells over the same period of time. Ratio images and graphical data from multiple dyes are displayed online.

When the assays of the invention are performed in a multi-well format, a suitable device for detecting changes in spectral qualities of the dyes used is a multi-well microplate reader. Suitable devices are commercially available, for example, from Molecular Devices (FLEXstation® microplate reader and fluid transfer system or FLIPR® system), from Hamamatsu (FDSS 6000) and the "VIPR" voltage ion probe reader (Aurora, Bioscience Corp. CA, USA). The FLIPR-Tetra™ is a second generation reader that provides real-time kinetic cell-based assays using up to 1536 simultaneous liquid transfer systems. All of these systems can be used with commercially available dyes such as FMP, which excites in the visible wavelength range.

Several commercial fluorescence detectors are available that can inject liquid into a single well or simultaneously into multiple wells. These include, but are not limited to, the Molecular Devices FlexStation™ (eight wells), BMG NovoStar (two wells) and Aurora VIPR™ (eight wells). Typically, these instruments require 12 to 96 minutes to read a 96-well plate in flash luminescence or fluorescence mode (1 min/well). Other endpoint microtiter fluorescent readers that may be used are the Perkin-Elmer Envision® and Labsystems Fluoroskan II. An alternative method is to inject the modulator into all sample wells at the same time and measure the luminescence in the whole plate by imaging with a charge-coupled device (CCD) camera, similar to the way that calcium responses are read by calcium-sensitive fluorescent dyes in the FLIPR®, FLIPR-384® or FLIPR-Tetra™ instruments. Other fluorescence imaging systems with integrated liquid handling are expected from other commercial suppliers such as the second generation LEADSEEKER from Amersham, the Perkin Elmer CellLux™ —Cellular Fluorescence Workstation and the Hamamatsu FDSS6000 System. These instruments can generally be configured to proper excitation and emission settings to read FMP dye ($540_{ex} \pm 15$ nm, $570_{em} \pm 15$ nm) and calcium dye ($490_{ex} \pm 15$ nm, $530_{em} \pm 15$ nm). The excitation/emission characteristics differ for each dye, therefore, the instruments are configured to detect the dye chosen for each assay.

Test Compounds

Test compounds employed in the screening methods of this invention include for example, without limitation, synthetic organic compounds, chemical compounds, naturally occurring products, polypeptides and peptides, nucleic acids, etc.

Essentially any chemical compound can be used as a potential modulator or ligand in the assays of the invention. Most often compounds dissolved in aqueous or organic (especially dimethyl sulfoxide- or DMSO-based) solutions are used. The assays are designed to screen large chemical libraries by automating the assay steps. The compounds are provided from any convenient source to the cells. The assays are typically run in parallel (e.g., in microtiter formats on microtiter plates in robotic assays with different test compounds in different wells on the same plate). It will be appreciated that there are many suppliers of chemical compounds, including ChemDiv (San Diego, Calif.), Sigma-Aldrich (St. Louis, Mo.), Fluka Chemika-Biochemica-Analytika (Buchs Switzerland) and the like.

"Modulating" as used herein includes any effect on the functional activity of non-desensitizing TRPM5. This includes blocking or inhibiting the activity of the channel in the presence of, or in response to, an appropriate stimulator. Alternatively, modulators may enhance the activity of the channel. "Enhance" as used herein, includes any increase in the functional activity of non-desensitizing TRPM5.

In one embodiment, the high throughput screening methods involve providing a small organic molecule or peptide library containing a large number of potential TRPM5 modulators. Such "chemical libraries" are then screened in one or more assays, as described herein, to identify those library members (chemical species or subclasses) that display a desired characteristic activity. The compounds thus identified can serve as conventional "lead compounds" or can themselves be used as potential or actual products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14:309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.; etc.).

Candidate agents, compounds, drugs, and the like encompass numerous chemical classes, though typically they are organic molecules, preferably small organic compounds having a molecular weight of more than 100 and less than about 10,000 daltons, preferably, less than about 2000 to 5000 daltons. Candidate compounds may comprise functional groups necessary for structural interaction with proteins and typically include at least an amine, carbonyl, hydroxyl or carboxyl group, preferably at least two of the functional chemical groups. The candidate compounds may comprise cyclical carbon or heterocyclic structures, and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

A variety of other reagents may be included in the screening assay according to the present invention. Such reagents include, but are not limited to, salts, solvents, neutral proteins, e.g. albumin, detergents, etc., which may be used to facilitate optimal protein-protein binding and/or to reduce non-specific or background interactions. Examples of solvents include, but are not limited to, dimethyl sulfoxide (DMSO), ethanol and acetone, and are generally used at a concentration of less than or equal to 1% (v/v) of the total assay volume. In addition, reagents that otherwise improve the efficiency of the assay, such as protease inhibitors, anti-microbial agents, etc.

may be used. Further, the mixture of components in the method may be added in any order that provides for the requisite binding.

The compounds identified using the disclosed assay are potentially useful as ingredients or flavorants in ingestible compositions, i.e., foods and beverages as wells as orally administered medicinals. Compounds that modulate taste perception can be used alone or in combination as flavorants in foods or beverages. The amount of such compound(s) will be an amount that yields the desired degree of modulated taste perception of which starting concentrations may generally be between 0.1 and 1000 µM.

EXAMPLES

Example 1

Imaging-Based High Throughput Screening Assay Using Transiently-Transfected Cells As described in greater detail below, HEK 293 cells, transiently transfected with a plasmid bearing a non-desensitizing hTRPM5, were used to develop a high throughput screening assay. Indirect measurement of the changes in $Na^+$ ions within the HEK 293 cells were made using a FMP dye and stimulation of the cells using calcium activating agents.

Plasmid Construction

First strand cDNA was synthesized by Thermoscript™ RT-PCR System (Invitrogen) from human small intestine poly A+RNA (BD Biosciences) and the full length hTRPM5 was amplified by PCR using GC Melt (BD Biosciences). The product was PCR purified by Pure Link™ PCR Purification (Invitrogen) and inserted into a vector using the TOPO TA Cloning®Kit (Invitrogen). After sequencing, 6 mutations were found and corrected using the Quick Change® Multi Site Directed Mutagenesis Kit (Stratagene) in 2 rounds of PCR. Three mutations were corrected in each round of PCR. The final hTRPM5 nucleotide sequence (SEQ ID NO: 1) is shown in FIG. 1. The full length hTRPM5 nucleotide sequence was excised from the TOPO® TA vector using the EcoRI and NotI restriction enzymes and ligated into the pENTR™ 3C vector (Invitrogen), which had also been digested with EcoRI and NotI. The insert and vector bands were gel extracted and purified using the SNAP™ Gel Purification Kit (Invitrogen). Finally, LR Recombination Reaction (Invitrogen) was used to insert the entry clone into destination vectors of interest (e.g., pT-Rex-DEST™-30, pcDNA-DEST™-53, pcDNA 3.2/v5-DEST™, pcDNA 6.2/V5-DEST™ and pcDNA-DEST™-26). The pcDNA-DEST™-26 (Invitrogen) destination vector already contains a hexahistidine tag that allows for the creation of an amino-terminal polyhistidine epitope tagged $(His)_6$-TRPM5 ion channel. Bacteria were transformed with the resulting pcDNA-DEST™-26-$(His)_6$-hTRPM5 vector now encoding amino-terminal polyhistidine epitope tagged hTRPM5. Transformed bacteria were grown in culture and subsequently lysed to confirm the presence of the nucleotide sequence encoding amino-terminal polyhistidine epitope tagged hTRPM5, through the isolation and subsequent restriction endonuclease digestion of plasmid DNA. FIGS. 2A and 2B. show the commercially available pcDNA-DEST-26™ vector used to carry the cDNA of the non-desensitizing TRPM5 ion channel and the resulting translated protein sequence (SEQ ID NO: 2) of the non-desensitizing $(His)_6$-TRPM5 ion channel.

Transfection $5.0 \times 10^6$ HEK 293 cells (ATCC) were plated in a 10 cm culture dish at 37° C. in a $CO_2$ incubator in Dulbecco's Modified Eagle's Medium (DMEM) supplemented with 10% Fetal Bovine Serum (FBS) and Penicillin-Streptomycin Solution. The following day, medium in the culture dish was exchanged with 15 mL of DMEM/10% FBS over a period of 3 hours. Prior to cell transfection, 24 µg of pcDNA-DEST-26-$(His)_6$-hTRPM5 was incubated in a 5 mL polypropylene tube for 5 minutes at room temperature in 1.5 mL of OPTI-MEM media (Invitrogen). In a separate 5 mL polypropylene tube, 42 µL of Lipofectamine™ 2000 (Invitrogen) was incubated for 5 minutes at room temperature in 1.5 mL of OPTI-MEM media. After the 5 minute incubation period, the pcDNA-DEST-26-$(His)_6$-hTRPM5 and Lipofectamine™ 2000 solutions were mixed together and incubated for an additional 20 minutes at room temperature. The entire mixture was then added to the dish containing naïve HEK 293 cells and 15 mL DMEM/10% FBS and incubated overnight at 37° C. in a $CO_2$ incubator. The following day, the cells were trypsinized and then plated on 384-well poly-D-lysine coated black clear bottom plates at 12,000 cells per well and incubated overnight at 37° C. in a $CO_2$ incubator overnight. Plates were then assayed on a FLIPR Tetra reader as described.

Membrane Potential Assay

100 µl of the Blue or Red FMP dye (Molecular Devices) was added to each well of plates seeded with HEK cells transiently transfected with pDEST-26™-$(His)_6$-hTRPM 5. The plate was then incubated in a 37° C. /5% $CO_2$ incubator for 1 hour. The plate was read in a FLEXStation™ microplate reader (Molecular Devices) with an excitation of 530 nm and an emission of 565 nm. The fluorescence was monitored for 3 minutes upon exposure of the cells to a calcium activating agent (carbachol, thrombin peptide or ATP).

Results

Figure 3:
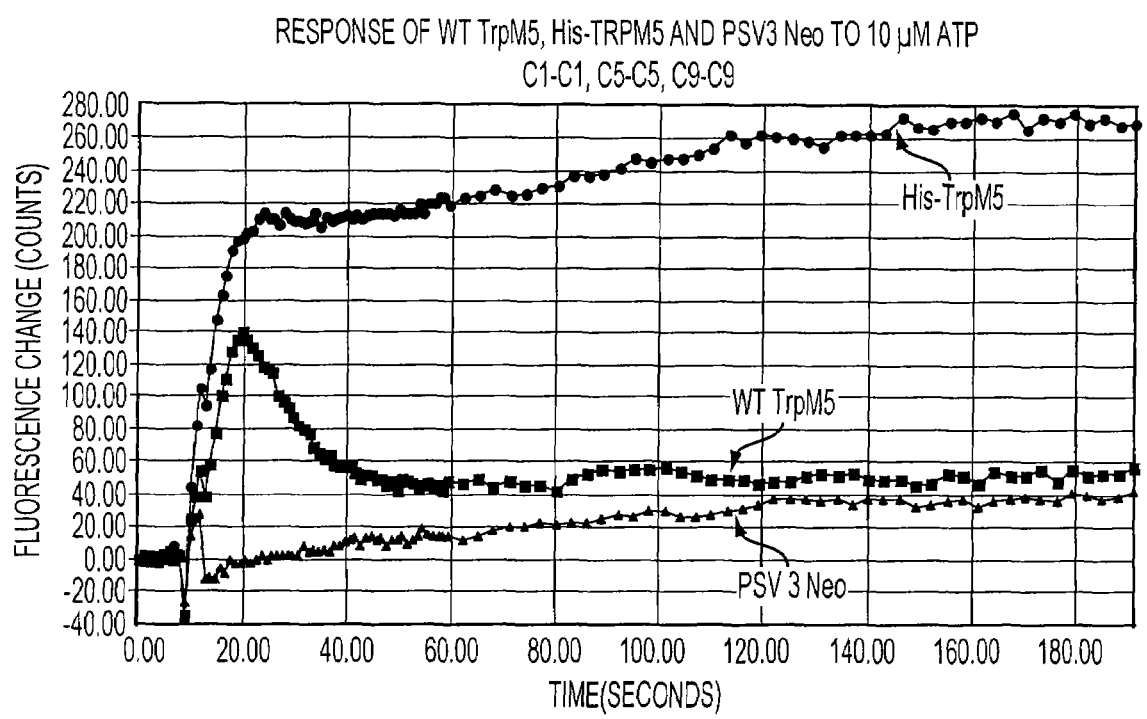
FIG. 3 shows the membrane potential response detected using a FLIPR® method in cells transfected with either wild-type (WT hTRPM5) hTRPM5 DNA, non-desensitizing ((His)$_6$-hTRPM5) or PSV3 Neo DNA to the application of 10 μM ATP. PSV3 Neo DNA is an empty vector that does not encode an ion channel and is used as the sham control.

The pDEST™-26-$(His)_6$-hTRPM5 plasmid was readily expressed as demonstrated below by providing a response to stimuli in contrast to untransfected parentals. Demonstration of TRPM5 response to stimuli is shown in FIG. 3. Cells transfected with either wildtype hTRPM5 DNA, non-desensitizing $(His)_6$-hTRPM5 DNA or PSV3 Neo were loaded with FMP dye and then treated with 10 µM ATP and monitored for an increase in cellular fluorescence in the FLEXstation™. The cells transfected with PSV3 Neo show no significant response to the application of ATP. Cells transfected with wildtype hTRPM5 DNA showed an initial activation of the ion channel as evidenced by an increase in fluorescence lasting about 30 seconds followed by rapid inactivation. Cells transfected with non-desensitizing $(His)_6$-hTRPM5 DNA showed an initial activation of the ion channel as evidenced by an increase in fluorescence. However, these non-desensitizing $(His)_6$-hTRPM5 cells do not exhibit a rapid inactivation of the ion channel and therefore fluorescence is observed at significant levels for more than 3 minutes. These results show that the non-desensitizing $(His)_6$-hTRPM 5 ion channel is useful for HTS assays that require a signal that lasts more than 30 seconds.

Example 2

Electrophysiology-Based High Throughput Screening Assay Using Transiently-Transfected Cells Whole-cell recordings of TRP channel currents were obtained from acutely trypsinized hTRPM5- and $(His)_6$-hTRPM5 expressing HEK 293 cells. The bath solution consisted of Hank's Balanced Salt solution comprising 1.2 mM $CaCl_2$, 0.5 mM $MgCl_2 \cdot 6H_2O$, 0.4 mM $MgSO_4 \cdot 7H_2O$, 5.3 mM KCl, 0.4 mM $KH_2PO_4$, 137.9 mM NaCl, 0.3 mM $Na_2HPO_4 \cdot 7H_2O$, and 5.5 mM D-Glucose, with 20 mM HEPES (Invitrogen), pH 7.4 (NaOH). The internal pipette solution contained 135 mM glutamic acid, 8 mM NaCl, 9 mM $CaCl_2$, 10 mM HEPES and 10 mM EGTA, pH 7.2 (CsOH) (Sigma). The calculated concentration of free calcium in the internal solution was 1.5 µM. Recording pipettes were pulled using a Flaming/Brown Micropipette Puller (Sutter Instruments), from fire-polished borosilicate glass, to approximately 2 MΩ. Voltage clamp recordings were obtained in whole cell mode using MultiClamp 700B amplifier and Digidata 1322A converter running on Clampex 9.2 software (Axon Instruments). Recordings were performed at room temperature. The recording protocol consisted of a ramp from −80 mV potential to +80 mV, followed by a step to −80 mV. Series resistance was automatically compensated immediately after the break-in. Data were filtered at 1 kHz and sampled at 5 kHz.

Demonstration of non-desensitizing $(His)_6$-hTRPM5 response to intracellular calcium increases is shown in FIG. 4. In panel A, cells transfected with wildtype hTRPM5-expressing HEK 293 cells show rapid activation followed by rapid inactivation as measured by changes in current. In panel B, non-desensitizing $(His)_6$-hTRPM5 expressing HEK 293 cells show rapid activation. In panel B, the current changes do not reflect a rapid inactivation. Increased current levels are sustained for more than 2 minutes. In practice of the art, the prolonged signal in FIG. 4B enables repeated addition of compounds during a stable current response.

Example 3

High Throughput Screening Assay Using Suboptimal Concentrations of Calcium-Activating Agents Specificity of potential TRPM5 activating compounds may be identified using suboptimal concentrations of agents that increase intracellular calcium levels. In this type of assay, rather than using a high concentration of, for example carbachol, a reduced concentration can be added to non-desensitizing $(His)_6$-hTRPM5-expressing cells with or without an additional test compound. Enhancers of TRPM5 activity are those test compounds that increase the fluorescent intensity in reduced carbachol treated cells, to the level seen in cells treated to a high dose.

A carbachol dose response curve can be generated for the non-desensitizing $(His)_6$-hTRPM5 expressing cells so that the suboptimal concentration range could be determined. Cells expressing non-desensitizing $(His)_6$-hTRPM5 can be incubated with an $EC_{20}$-$EC_{30}$ level of carbachol (0.3 to 1 µM) prior to addition of test compounds. Mock incubated and $EC_{100}$ treated cells can be used as controls. Test compounds that increase the fluorescent intensity of $EC_{20}$-$EC_{30}$ treated cells to levels approaching $EC_{100}$ treated cells can be classified as activators of TRPM5.

Example 4

KCl Counterscreen for TRPM5 Specificity

KCl activates a number of ion channels, but not TRPM5. Therefore, KCl can be used as a counterscreen to identify modulating compounds specific for TRPM5.

The ideal blocker would block non-desensitizing TRPM5 but not other channels. The TRPM5 assay can be conducted as described in Example 3, utilizing a membrane potential dye. A test compound can be added, and the cells are then stimulated with ATP to trigger the channel, leading to a dye response. The process is shown schematically in FIG. 5. The KCl counterscreen can be performed as described in Example 3, with identical cells, pretreated with the same compound, but the stimulus is 20 mM KCl, not ATP.

The KCl counterscreen is also useful for the identification of selective TRPM5 enhancing compounds.

Example 5

Effects of Enhancer Compounds on Non-Desensitizing $(His)_6$-hTRPM5

Cells transfected with non-desensitizing $(His)_6$-hTRPM5 DNA were loaded with FMP dye and then treated with 10 µM ATP and monitored for an increase in cellular fluorescence in the FLEXstation™. Fluorescence, as recorded in relative light units, for the High Control (10 µM ATP) is shown in blue in FIG. 6. Fluorescence, recorded in relative light units, for the combined application of an enhancer compound, LG6900431, and the High Control is shown in green in FIG. 6. The additional application of the enhancer compound to the non-desensitizing $(His)_6$-hTRPM5 ion channel produced an increase in relative light units measured. As in the case of the High Control, the enhancer/High Control application resulted in the non-desensitizing $(His)_6$-hTRPM5 remaining open for at least 100 seconds.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All publications, patents and patent applications cited herein are incorporated by reference in their entirety into the disclosure.

What is claimed is:

1. An isolated polynucleotide, wherein the polynucleotide has the sequence of SEQ ID NO: 1.
2. An isolated polynucleotide, wherein the polynucleotide encodes a non-desensitizing TRPM5 ion channel having the sequence of SEQ ID NO: 2.
3. A recombinant vector comprising the isolated polynucleotide of claim 1.
4. A recombinant vector comprising the isolated polynucleotide of claim 2.
5. An isolated host cell comprising the vector of claim 3.
6. A method of making an isolated polypeptide comprising: (a) culturing the host cell of claim 5 under conditions such that said polypeptide is expressed; and (b) recovering said polypeptide.
7. An isolated host cell comprising the vector of claim 4.
8. A method of making an isolated polypeptide comprising: (a) culturing the host cell of claim 7 under conditions such that said polypeptide is expressed; and (b) recovering said polypeptide.

* * * * *